United States Patent
Horseman et al.

(10) Patent No.: US 9,722,472 B2
(45) Date of Patent: Aug. 1, 2017

(54) SYSTEMS, COMPUTER MEDIUM AND COMPUTER-IMPLEMENTED METHODS FOR HARVESTING HUMAN ENERGY IN THE WORKPLACE

(71) Applicant: Saudi Arabian Oil Company, Dhahran (SA)

(72) Inventors: Samantha Horseman, Dhahran (SA); Ronald Monsen, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 903 days.

(21) Appl. No.: 14/102,619

(22) Filed: Dec. 11, 2013

(65) Prior Publication Data

US 2015/0162802 A1 Jun. 11, 2015

(51) Int. Cl.

| | | |
|---|---|---|
| F02B 63/04 | (2006.01) | |
| F03G 7/08 | (2006.01) | |
| H02K 7/18 | (2006.01) | |
| G05B 15/02 | (2006.01) | |
| G06F 19/00 | (2011.01) | |

(Continued)

(52) U.S. Cl.
CPC ........... H02K 7/1861 (2013.01); G05B 15/02 (2013.01); G06F 19/3481 (2013.01); G06Q 50/06 (2013.01); G06Q 50/20 (2013.01); G06Q 50/22 (2013.01)

(58) Field of Classification Search
USPC .................................. 290/1 R, 4 R; 600/301
See application file for complete search history.

(56) References Cited

U.S. PATENT DOCUMENTS

| | | |
|---|---|---|
| 5,000,188 A | 3/1991 | Kojima |
| 5,253,656 A | 10/1993 | Rincoe et al. |

(Continued)

FOREIGN PATENT DOCUMENTS

| | | |
|---|---|---|
| AU | 767533 | 11/2003 |
| CN | 101065752 A | 10/2007 |

(Continued)

OTHER PUBLICATIONS

"Footrests—Adjustable Footrest Solutions for the Office", Ergo in Demand, Aug. 20, 2009, pp. 1-4, Ergo in Demand Inc., www.ergoindemand.com/footrest.html.

(Continued)

*Primary Examiner* — Pedro J Cuevas
(74) *Attorney, Agent, or Firm* — Bracewell LLP; Constance G. Rhebergen; Christopher L. Drymalla

(57) ABSTRACT

Provided are embodiments of systems, computer medium and computer-implemented methods for harvesting human energy from an employee. The techniques including determining an amount of energy harvested, and selectively enabling/disabling one or more electronic user devices based at least in part on the amount of energy harvested. The amount of energy harvested including kinetic energy and neural energy. The kinetic energy having been harvested by a kinetic energy system including one or more kinetic energy harvesting devices that harvest kinetic energy generated by physical activity of an employee. The neural energy having been harvested by a neural energy system that includes one or more neural energy harvesting devices that harvest neural energy generated by neural activity of the employee.

23 Claims, 10 Drawing Sheets

(51) Int. Cl.
   *G06Q 50/06*  (2012.01)
   *G06Q 50/20*  (2012.01)
   *G06Q 50/22*  (2012.01)
   *F01C 13/00*  (2006.01)
   *F01D 15/10*  (2006.01)

(56) References Cited

U.S. PATENT DOCUMENTS

| | | |
|---|---|---|
| 5,304,112 A | 4/1994 | Mrklas et al. |
| 5,305,238 A | 4/1994 | Starr, III |
| 5,331,549 A | 7/1994 | Crawford, Jr. |
| 5,343,869 A | 9/1994 | Pross et al. |
| 5,410,471 A | 4/1995 | Alyfuku et al. |
| 5,435,315 A | 7/1995 | McPhee et al. |
| 5,441,047 A | 8/1995 | David |
| 5,542,420 A | 8/1996 | Goldman et al. |
| 5,570,301 A | 10/1996 | Barrus |
| 5,626,145 A | 5/1997 | Clapp et al. |
| 5,673,691 A | 10/1997 | Abrams et al. |
| 5,792,047 A | 8/1998 | Coggins |
| 5,813,993 A | 9/1998 | Kaplan et al. |
| 5,937,387 A | 8/1999 | Summerell et al. |
| 6,033,344 A | 3/2000 | Trulaske et al. |
| 6,049,281 A | 4/2000 | Osterweil |
| 6,083,156 A | 7/2000 | Lisiecki |
| 6,104,296 A | 8/2000 | Yasushi et al. |
| 6,148,280 A | 11/2000 | Kramer |
| 6,149,586 A | 11/2000 | Elkind |
| 6,190,314 B1 | 2/2001 | Ark et al. |
| 6,203,495 B1 | 3/2001 | Bardy |
| 6,269,339 B1 | 7/2001 | Silver |
| 6,281,594 B1 | 8/2001 | Sarich |
| 6,291,900 B1 | 9/2001 | Tiemann et al. |
| 6,293,771 B1 | 9/2001 | Haney et al. |
| 6,307,476 B1 | 10/2001 | Smith et al. |
| 6,309,342 B1 | 10/2001 | Blazey et al. |
| 6,334,837 B1 | 1/2002 | Hein et al. |
| 6,369,337 B1 | 4/2002 | Machiyama |
| 6,381,577 B1 | 4/2002 | Brown |
| 6,408,263 B1 | 6/2002 | Summers |
| 6,425,862 B1 | 7/2002 | Brown |
| 6,450,530 B1 | 9/2002 | Frasher et al. |
| 6,452,862 B1 | 9/2002 | Tomotani |
| 6,546,286 B2 | 4/2003 | Olson |
| 6,572,558 B2 | 6/2003 | Masakov et al. |
| 6,585,645 B2 | 7/2003 | Hutchinson |
| 6,646,556 B1 | 11/2003 | Smith et al. |
| 6,648,820 B1 | 11/2003 | Sarel |
| 6,658,572 B1 | 12/2003 | Craig |
| 6,669,286 B2 | 12/2003 | Iusim |
| 6,673,027 B2 | 1/2004 | Fischer |
| 6,675,130 B2 | 1/2004 | Kanevsky et al. |
| 6,692,258 B1 | 2/2004 | Kurzweil |
| 6,736,642 B2 | 5/2004 | Bajer |
| 6,768,246 B2 | 7/2004 | Pelrine et al. |
| 6,781,067 B2 | 8/2004 | Montagnino et al. |
| 6,828,908 B2 | 12/2004 | Clark |
| 6,832,987 B2 | 12/2004 | David et al. |
| 6,850,798 B2 | 2/2005 | Morgan |
| 6,918,769 B2 | 7/2005 | Rink |
| 6,931,359 B2 | 8/2005 | Tamada |
| 6,982,497 B2 | 1/2006 | Rome |
| 7,005,757 B2 | 2/2006 | Pandian |
| 7,027,621 B1 | 4/2006 | Prokoski |
| 7,074,198 B2 | 7/2006 | Krullaards |
| 7,109,872 B2 | 9/2006 | Balaban et al. |
| 7,128,577 B2 | 10/2006 | Renaud |
| 7,152,024 B2 | 12/2006 | Marschner |
| 7,155,158 B1 | 12/2006 | Iuppa |
| 7,163,489 B1 | 1/2007 | Nelson |
| 7,188,151 B2 | 3/2007 | Kumar et al. |
| 7,233,312 B2 | 6/2007 | Stern et al. |
| 7,273,453 B2 | 9/2007 | Shallenberger |
| 7,304,580 B2 | 12/2007 | Sullivan et al. |
| 7,315,249 B2 | 1/2008 | Littell |
| 7,351,206 B2 | 4/2008 | Suzuki |
| 7,399,276 B1 | 7/2008 | Brown et al. |
| 7,407,484 B2 | 8/2008 | Korman |
| 7,481,779 B2 | 1/2009 | Large |
| 7,598,881 B2 | 10/2009 | Morgan |
| 7,624,037 B2 | 11/2009 | Bost |
| 7,652,582 B2 | 1/2010 | Littell |
| 7,689,271 B1 | 3/2010 | Sullivan |
| 7,771,318 B2 | 8/2010 | Narayanaswami |
| 7,830,249 B2 | 11/2010 | Dorneich et al. |
| 7,844,347 B2 | 11/2010 | Brabec |
| 7,849,115 B2 | 12/2010 | Reiner |
| 7,901,324 B2 | 3/2011 | Kodama |
| 7,958,002 B2 | 6/2011 | Bost |
| 7,972,266 B2 | 7/2011 | Gobeyn et al. |
| 8,015,022 B2 | 9/2011 | Gore |
| 8,018,346 B2 | 9/2011 | Gottlieb et al. |
| 8,019,121 B2 | 9/2011 | Marks |
| 8,021,298 B2 | 9/2011 | Baird |
| 8,024,202 B2 | 9/2011 | Carroll |
| 8,030,786 B2 | 10/2011 | Jackson et al. |
| 8,038,615 B2 | 10/2011 | Gobeyn |
| 8,081,083 B2 | 12/2011 | Hinterlong |
| 8,092,226 B2 | 1/2012 | Findlay |
| 8,095,641 B2 | 1/2012 | Aggarwal et al. |
| 8,103,333 B2 | 1/2012 | Tran |
| 8,180,457 B2 | 5/2012 | Matos |
| 8,203,454 B2 | 6/2012 | Knight et al. |
| 8,235,895 B2 | 8/2012 | David |
| 8,308,562 B2 | 11/2012 | Patton |
| 8,428,962 B1 | 4/2013 | Brinkley et al. |
| 8,477,039 B2 | 7/2013 | Gleckler et al. |
| 8,487,456 B2 | 7/2013 | Donelan et al. |
| 8,597,121 B2 | 12/2013 | Andres Del Valle |
| 8,612,247 B2 | 12/2013 | Sawano |
| 8,636,670 B2 | 1/2014 | Ferren et al. |
| 8,738,129 B2 | 5/2014 | Packer |
| 8,775,196 B2 | 7/2014 | Simpson et al. |
| 8,956,292 B2 | 2/2015 | Wekell et al. |
| 9,256,711 B2 * | 2/2016 | Horseman ............ G06F 19/3406 |
| 9,462,977 B2 * | 10/2016 | Horseman ............ G06F 19/3418 |
| 9,492,120 B2 * | 11/2016 | Horseman ............ G06F 19/3418 |
| 9,526,455 B2 * | 12/2016 | Horseman ............ G06F 19/3418 |
| 9,615,746 B2 * | 4/2017 | Horseman ............ A61B 5/0008 |
| 2001/0039372 A1 | 11/2001 | Yasushi et al. |
| 2001/0040591 A1 | 11/2001 | Abbott et al. |
| 2001/0041845 A1 | 11/2001 | Kim |
| 2001/0042004 A1 | 11/2001 | Taub |
| 2002/0050924 A1 | 5/2002 | Mahbub |
| 2002/0062069 A1 | 5/2002 | Mault |
| 2002/0077534 A1 | 6/2002 | DuRousseau |
| 2002/0087093 A1 | 7/2002 | Chai |
| 2002/0095099 A1 | 7/2002 | Quyen et al. |
| 2002/0132092 A1 | 9/2002 | Wagner |
| 2002/0156351 A1 | 10/2002 | Sagel |
| 2002/0167486 A1 | 11/2002 | Tan et al. |
| 2002/0183644 A1 | 12/2002 | Levendowski et al. |
| 2002/0193707 A1 | 12/2002 | Atlas et al. |
| 2003/0058111 A1 | 3/2003 | Lee et al. |
| 2003/0073552 A1 | 4/2003 | Knight |
| 2003/0113698 A1 | 6/2003 | Von Der Geest |
| 2003/0154107 A1 | 8/2003 | Medvedeff |
| 2003/0163351 A1 | 8/2003 | Brown et al. |
| 2003/0201978 A1 | 10/2003 | Lee et al. |
| 2003/0204130 A1 | 10/2003 | Colston, Jr. et al. |
| 2003/0209113 A1 | 11/2003 | Brooks et al. |
| 2003/0212579 A1 | 11/2003 | Brown et al. |
| 2003/0222440 A1 | 12/2003 | Basir |
| 2003/0226695 A1 | 12/2003 | Mault |
| 2004/0002634 A1 | 1/2004 | Nihtila |
| 2004/0015191 A1 | 1/2004 | Otman |
| 2004/0095378 A1 | 5/2004 | Vigue |
| 2004/0148140 A1 | 7/2004 | Tarassenko et al. |
| 2004/0152956 A1 | 8/2004 | Korman |
| 2004/0162466 A1 | 8/2004 | Quy |
| 2004/0167381 A1 | 8/2004 | Lichter et al. |
| 2004/0193068 A1 | 9/2004 | Burton et al. |
| 2004/0195876 A1 | 10/2004 | Huiban |
| 2004/0214148 A1 | 10/2004 | Salvino et al. |

(56) References Cited

U.S. PATENT DOCUMENTS

| | | |
|---|---|---|
| 2004/0222892 A1 | 11/2004 | Balaban |
| 2004/0242976 A1 | 12/2004 | Abreu |
| 2004/0260156 A1 | 12/2004 | David |
| 2005/0075542 A1 | 4/2005 | Goldreich |
| 2005/0101845 A1 | 5/2005 | Nihtila |
| 2005/0108086 A1 | 5/2005 | Kosman |
| 2005/0124864 A1 | 6/2005 | Mack et al. |
| 2005/0164833 A1 | 7/2005 | Florio |
| 2005/0181347 A1 | 8/2005 | Barnes |
| 2005/0250996 A1 | 11/2005 | Shirai et al. |
| 2005/0260548 A1 | 11/2005 | Nava |
| 2005/0273890 A1 | 12/2005 | Flaherty et al. |
| 2006/0001545 A1 | 1/2006 | Wolf |
| 2006/0026036 A1 | 2/2006 | Mahmood |
| 2006/0030783 A1 | 2/2006 | Tsai et al. |
| 2006/0074708 A1 | 4/2006 | Woods |
| 2006/0122863 A1 | 6/2006 | Gottesman et al. |
| 2006/0135857 A1 | 6/2006 | Ho et al. |
| 2006/0155175 A1 | 7/2006 | Ogino et al. |
| 2006/0183980 A1 | 8/2006 | Yang |
| 2006/0203991 A1 | 9/2006 | Kramer et al. |
| 2006/0240395 A1 | 10/2006 | Faist et al. |
| 2006/0241977 A1 | 10/2006 | Fitzgerald et al. |
| 2006/0253303 A1 | 11/2006 | Brown |
| 2006/0267747 A1 | 11/2006 | Kondo |
| 2006/0287883 A1 | 12/2006 | Turgiss et al. |
| 2007/0004969 A1 | 1/2007 | Kong et al. |
| 2007/0011273 A1 | 1/2007 | Greenstein et al. |
| 2007/0016449 A1 | 1/2007 | Cohen et al. |
| 2007/0017531 A1 | 1/2007 | Large |
| 2007/0038153 A1 | 2/2007 | Basson et al. |
| 2007/0050715 A1 | 3/2007 | Behar |
| 2007/0055185 A1 | 3/2007 | Trandafir et al. |
| 2007/0055549 A1 | 3/2007 | Moore et al. |
| 2007/0083384 A1 | 4/2007 | Geslak et al. |
| 2007/0118398 A1 | 5/2007 | Perls |
| 2007/0136093 A1 | 6/2007 | Rankin |
| 2007/0139362 A1 | 6/2007 | Colton et al. |
| 2007/0146131 A1 | 6/2007 | Boverie |
| 2007/0179360 A1 | 8/2007 | Mikat |
| 2007/0191727 A1 | 8/2007 | Fadem |
| 2007/0193811 A1 | 8/2007 | Breed et al. |
| 2007/0219419 A1 | 9/2007 | KenKnight et al. |
| 2007/0225118 A1 | 9/2007 | Giorno |
| 2007/0225585 A1 | 9/2007 | Washbon et al. |
| 2007/0244724 A1 | 10/2007 | Pendergast et al. |
| 2007/0270909 A1 | 11/2007 | Saketkhou |
| 2007/0276202 A1 | 11/2007 | Raisanen et al. |
| 2007/0282177 A1 | 12/2007 | Pilz |
| 2007/0299325 A1 | 12/2007 | Farrell et al. |
| 2008/0001735 A1 | 1/2008 | Tran |
| 2008/0001736 A1 | 1/2008 | Steadman et al. |
| 2008/0015422 A1 | 1/2008 | Wessel |
| 2008/0052837 A1 | 3/2008 | Blumberg |
| 2008/0140140 A1 | 6/2008 | Grimley |
| 2008/0146892 A1 | 6/2008 | LeBoeuf et al. |
| 2008/0150889 A1 | 6/2008 | Stern |
| 2008/0161654 A1 | 7/2008 | Teller et al. |
| 2008/0171914 A1 | 7/2008 | Ouwerkerk et al. |
| 2008/0177158 A1 | 7/2008 | Teller et al. |
| 2008/0177341 A1 | 7/2008 | Bowers |
| 2008/0177614 A1 | 7/2008 | An et al. |
| 2008/0177836 A1 | 7/2008 | Bennett |
| 2008/0188777 A1 | 8/2008 | Bedziouk |
| 2008/0193905 A1 | 8/2008 | Leung |
| 2008/0194995 A1 | 8/2008 | Grady-Van Den Nieuwboer |
| 2008/0200774 A1 | 8/2008 | Luo |
| 2008/0218331 A1 | 9/2008 | Baillot |
| 2008/0228046 A1 | 9/2008 | Futatsuyama et al. |
| 2008/0242521 A1 | 10/2008 | Einav |
| 2008/0242951 A1 | 10/2008 | Jung et al. |
| 2008/0242952 A1 | 10/2008 | Jung et al. |
| 2008/0304712 A1 | 12/2008 | Rowe et al. |
| 2008/0306357 A1 | 12/2008 | Korman |
| 2008/0306762 A1 | 12/2008 | James |
| 2009/0002178 A1 | 1/2009 | Guday et al. |
| 2009/0030290 A1 | 1/2009 | Kozuch et al. |
| 2009/0030767 A1 | 1/2009 | Morris et al. |
| 2009/0040196 A1 | 2/2009 | Duckstein |
| 2009/0047644 A1 | 2/2009 | Mensah |
| 2009/0047645 A1 | 2/2009 | Dibenedetto et al. |
| 2009/0055204 A1 | 2/2009 | Pennington et al. |
| 2009/0058661 A1 | 3/2009 | Glecker et al. |
| 2009/0149721 A1 | 6/2009 | Yang |
| 2009/0149799 A1 | 6/2009 | Dacey, Jr. et al. |
| 2009/0156888 A1 | 6/2009 | Su et al. |
| 2009/0160640 A1 | 6/2009 | Leung et al. |
| 2009/0173549 A1 | 7/2009 | Lev |
| 2009/0177688 A1 | 7/2009 | Karlsen et al. |
| 2009/0178858 A1 | 7/2009 | Daniels et al. |
| 2009/0198521 A1 | 8/2009 | Barker |
| 2009/0209829 A1 | 8/2009 | Yanagidaira et al. |
| 2009/0216558 A1 | 8/2009 | Reisman et al. |
| 2009/0231145 A1 | 9/2009 | Wada et al. |
| 2009/0287101 A1 | 11/2009 | Ferren et al. |
| 2009/0287191 A1 | 11/2009 | Ferren |
| 2009/0300616 A1 | 12/2009 | Sicurello et al. |
| 2009/0307025 A1 | 12/2009 | Menon |
| 2009/0319297 A1 | 12/2009 | Hernandez et al. |
| 2010/0010365 A1 | 1/2010 | Terao et al. |
| 2010/0014711 A1 | 1/2010 | Camhi et al. |
| 2010/0049004 A1 | 2/2010 | Edman et al. |
| 2010/0049541 A1 | 2/2010 | Pollard et al. |
| 2010/0131283 A1 | 5/2010 | Linthicum et al. |
| 2010/0169118 A1 | 7/2010 | Rottsolk et al. |
| 2010/0169219 A1 | 7/2010 | Sellers et al. |
| 2010/0205541 A1 | 8/2010 | Rapaport et al. |
| 2010/0225489 A1 | 9/2010 | Hinterlong |
| 2010/0240458 A1 | 9/2010 | Gaiba et al. |
| 2010/0259043 A1 | 10/2010 | Balsamo |
| 2010/0261978 A1 | 10/2010 | Lithgow |
| 2010/0283265 A1 | 11/2010 | Rastegar et al. |
| 2010/0286567 A1 | 11/2010 | Wolfe et al. |
| 2010/0293267 A1 | 11/2010 | Ribak et al. |
| 2010/0298656 A1 | 11/2010 | McCombie et al. |
| 2010/0299257 A1 | 11/2010 | Turk |
| 2010/0305480 A1 | 12/2010 | Fu et al. |
| 2010/0312606 A1 | 12/2010 | Gala |
| 2010/0332250 A1 | 12/2010 | Simpson |
| 2011/0033830 A1 | 2/2011 | Cherian |
| 2011/0035231 A1 | 2/2011 | Firminger et al. |
| 2011/0046688 A1 | 2/2011 | Schwibner |
| 2011/0055720 A1 | 3/2011 | Potter et al. |
| 2011/0060252 A1 | 3/2011 | Simonsen et al. |
| 2011/0080290 A1 | 4/2011 | Baxi et al. |
| 2011/0098056 A1 | 4/2011 | Rhoads et al. |
| 2011/0119075 A1 | 5/2011 | Dhoble |
| 2011/0125662 A1 | 5/2011 | Perry et al. |
| 2011/0137211 A1 | 6/2011 | Weisberg |
| 2011/0137669 A1 | 6/2011 | Bennett |
| 2011/0152635 A1 | 6/2011 | Morris et al. |
| 2011/0152696 A1 | 6/2011 | Ryan |
| 2011/0161100 A1 | 6/2011 | Peak et al. |
| 2011/0172744 A1 | 7/2011 | Davis et al. |
| 2011/0183305 A1 | 7/2011 | Orbach |
| 2011/0196212 A1 | 8/2011 | Peters et al. |
| 2011/0201960 A1 | 8/2011 | Price |
| 2011/0213664 A1 | 9/2011 | Osterhout et al. |
| 2011/0238591 A1 | 9/2011 | Kerr et al. |
| 2011/0257537 A1 | 10/2011 | Alatriste |
| 2011/0269601 A1 | 11/2011 | Nelson et al. |
| 2011/0275939 A1 | 11/2011 | Walsh et al. |
| 2011/0285146 A1 | 11/2011 | Kozinsky et al. |
| 2011/0295656 A1 | 12/2011 | Venkatasubramanian et al. |
| 2012/0007367 A1 | 1/2012 | Chang |
| 2012/0010488 A1 | 1/2012 | Henry et al. |
| 2012/0035433 A1 | 2/2012 | Chance |
| 2012/0052971 A1 | 3/2012 | Bentley |
| 2012/0071731 A1 | 3/2012 | Gottesman |
| 2012/0086249 A1 | 4/2012 | Hotary et al. |
| 2012/0117020 A1 | 5/2012 | Davis et al. |
| 2012/0122430 A1 | 5/2012 | Hutchings et al. |
| 2012/0127157 A1 | 5/2012 | Adler |
| 2012/0139731 A1 | 6/2012 | Razoumov et al. |

(56) References Cited

U.S. PATENT DOCUMENTS

| | | |
|---|---|---|
| 2012/0143031 A1 | 6/2012 | Belalcazar et al. |
| 2012/0146795 A1 | 6/2012 | Margon et al. |
| 2012/0154277 A1 | 6/2012 | Bar-Zeev et al. |
| 2012/0203465 A1 | 8/2012 | Callewaert et al. |
| 2012/0203491 A1 | 8/2012 | Sun et al. |
| 2012/0215076 A1 | 8/2012 | Yang et al. |
| 2012/0215976 A1 | 8/2012 | Inoue |
| 2012/0253484 A1 | 10/2012 | Burich et al. |
| 2012/0271121 A1 | 10/2012 | Della Torre et al. |
| 2012/0271143 A1 | 10/2012 | Aragones et al. |
| 2012/0290215 A1 | 11/2012 | Adler |
| 2012/0323590 A1 | 12/2012 | Udani |
| 2013/0009761 A1 | 1/2013 | Horseman |
| 2013/0009993 A1 | 1/2013 | Horseman |
| 2013/0011819 A1 | 1/2013 | Horseman |
| 2013/0012786 A1 | 1/2013 | Horseman |
| 2013/0012787 A1 | 1/2013 | Horseman |
| 2013/0012788 A1 | 1/2013 | Horseman |
| 2013/0012789 A1 | 1/2013 | Horseman |
| 2013/0012790 A1 | 1/2013 | Horseman |
| 2013/0012802 A1 | 1/2013 | Horseman |
| 2013/0013327 A1 | 1/2013 | Horseman |
| 2013/0013331 A1 | 1/2013 | Horseman |
| 2013/0056981 A1 | 3/2013 | Mullins et al. |
| 2013/0097093 A1 | 4/2013 | Kolber et al. |
| 2013/0158423 A1 | 6/2013 | Kapoor |
| 2013/0178960 A1 | 7/2013 | Sheehan et al. |
| 2013/0234826 A1 | 9/2013 | Sekiguchi et al. |
| 2013/0289889 A1 | 10/2013 | Yuen et al. |
| 2013/0297219 A1 | 11/2013 | Bangera et al. |
| 2013/0297344 A1 | 11/2013 | Cosentino et al. |
| 2014/0019165 A1* | 1/2014 | Horseman ........... G06F 19/3418 705/3 |
| 2014/0025396 A1* | 1/2014 | Horseman ........... G06F 19/3418 705/2 |
| 2014/0025397 A1* | 1/2014 | Horseman ........... G06F 19/3418 705/2 |
| 2014/0107718 A1 | 4/2014 | Foote |
| 2014/0129401 A1 | 5/2014 | Kruz et al. |
| 2014/0163330 A1* | 6/2014 | Horseman ........... A61B 5/6887 600/301 |
| 2014/0163331 A1* | 6/2014 | Horseman ........... G06F 19/3418 600/301 |
| 2014/0163332 A1* | 6/2014 | Horseman ........... G06F 19/3418 600/301 |
| 2014/0163333 A1* | 6/2014 | Horseman ........... A61B 5/6887 600/301 |
| 2014/0163335 A1* | 6/2014 | Horseman ........... G06F 19/3418 600/301 |
| 2014/0163336 A1* | 6/2014 | Horseman ........... G06F 19/3418 600/301 |
| 2014/0163337 A1* | 6/2014 | Horseman ........... A61B 5/6887 600/301 |
| 2014/0172461 A1 | 6/2014 | Rogers |
| 2015/0025928 A1 | 1/2015 | Kang et al. |
| 2015/0222096 A1 | 8/2015 | Nakayama |
| 2015/0226177 A1* | 8/2015 | DeFrank ................ A01G 25/16 700/284 |
| 2015/0257643 A1* | 9/2015 | Watson ................ A61B 5/0002 600/301 |
| 2015/0338265 A1 | 11/2015 | Carreel et al. |
| 2015/0375028 A1* | 12/2015 | Oteman ............. A63B 21/0628 482/2 |

FOREIGN PATENT DOCUMENTS

| | | |
|---|---|---|
| CN | 101115438 A | 1/2008 |
| CN | 201127606 Y | 10/2008 |
| CN | 101454050 A | 6/2009 |
| CN | 101930125 A | 12/2010 |
| DE | 102005048496 A1 | 4/2007 |
| EP | 1407713 A1 | 9/2008 |
| EP | 2151355 A1 | 2/2010 |
| EP | 2248461 A2 | 11/2010 |
| JP | 05-049603 A | 3/1993 |
| JP | H07204168 A | 8/1995 |
| JP | H10312241 A | 11/1998 |
| JP | H11328593 A | 11/1999 |
| JP | 2000037357 A | 2/2000 |
| JP | 2000342537 A | 12/2000 |
| JP | 2001187030 A | 7/2001 |
| JP | 2001209717 A | 8/2001 |
| JP | 2001356849 A | 12/2001 |
| JP | 2002109061 A | 4/2002 |
| JP | 2002159052 A | 5/2002 |
| JP | 2002215880 A | 8/2002 |
| JP | 2002259120 A | 9/2002 |
| JP | 2002291952 A | 10/2002 |
| JP | 2003070774 A | 3/2003 |
| JP | 2003091598 A | 3/2003 |
| JP | 2003521972 A | 7/2003 |
| JP | 2003235813 A | 8/2003 |
| JP | 2003247991 A | 9/2003 |
| JP | 2003256578 A | 9/2003 |
| JP | 2003310580 A | 11/2003 |
| JP | 2004113581 A | 4/2004 |
| JP | 2004135829 A | 5/2004 |
| JP | 3109753 U | 6/2005 |
| JP | 2005287688 A | 10/2005 |
| JP | 2005321869 A | 11/2005 |
| JP | 2006085262 A | 3/2006 |
| JP | 2006106952 A | 4/2006 |
| JP | 2006178805 A | 7/2006 |
| JP | 2008099834 A | 1/2008 |
| JP | 2008110032 A | 5/2008 |
| JP | 2008178546 A | 8/2008 |
| JP | 2008230366 A | 10/2008 |
| JP | 2008264188 A | 11/2008 |
| JP | 2008304978 A | 12/2008 |
| JP | 2009171544 A | 7/2009 |
| JP | 2009532072 A | 9/2009 |
| JP | 2009301360 A | 12/2009 |
| JP | 2010003070 A | 1/2010 |
| JP | 2010181324 A | 8/2010 |
| JP | 2010538701 A | 12/2010 |
| JP | 2011067708 A | 4/2011 |
| JP | 2011120787 A | 6/2011 |
| JP | 2011123579 A | 6/2011 |
| WO | 9601585 A1 | 1/1996 |
| WO | 0128416 A1 | 4/2001 |
| WO | 0186403 A1 | 11/2001 |
| WO | 0186403 A2 | 11/2001 |
| WO | 2005064447 A2 | 7/2005 |
| WO | 2006022465 A1 | 3/2006 |
| WO | 2007016056 A2 | 2/2007 |
| WO | 2007130591 A2 | 11/2007 |
| WO | 2008044325 A1 | 4/2008 |
| WO | 2010048145 A1 | 4/2010 |
| WO | 2010051037 A1 | 5/2010 |
| WO | 2010067275 A1 | 6/2010 |
| WO | 2011020299 A1 | 2/2011 |
| WO | WO2014023422 A1 | 2/2014 |

OTHER PUBLICATIONS

Berger et al., "Investing in Healthy Human Capital", Journal of Occupational Environmental Medicine vol. 45, No. 12, dated Dec. 2003; pp. 1213-1225.

Brown et al., "Prowess Proactive Wellness Environment Support System", Dec. 10, 2009, pp. 1-19, www.hsi.gatech.edu/onsitecenter/index.php/PROWESS.

Campbell et al., "The Rise of People-Centric Sensing", IEEE Computer Society, 2008, pp. 12-21, IEEE.

Georgia Tech, "Prowess Proactive Wellness Environment Support System", Dec. 12, 2009, pp. 1-27, www.hsi.gatech.edu/onsitecenter/index.php/PROWESS.

Goetzel et al., "Estimating the Return-on-Investment From Changes in Employee Health Risks on The Dow Chemical Company's Health Care Costs", Journal of Occupational Environmental Medicine vol. 47, No. 8, dated Aug. 2005; pp. 759-768.

(56) References Cited

OTHER PUBLICATIONS

Goetzel et al., "Health, Absence, Disability, and Presenteeism Cost Estimates of Certain Physical and Mental Health Conditions Affecting U.S. Employers", Journal of Occupational Environmental Medicine vol. 46, No. 4, dated Apr. 2004; pp. 398-412.
Goetzel et al., "Second-Year Results of an Obesity Prevention Program at The Dow Chemical Company", Journal of Occupational Environmental Medicine vol. 52, No. 3, dated Mar. 2010; pp. 291-302.
Goetzel et al., "The Health and Productivity Cost Burden of the "Top 10" Physical and Mental Health Conditions Affecting Six Large U.S. Employers in 1999", Journal of Occupational Environmental Medicine vol. 45, No. 1, dated Jan. 2003; pp. 5-14.
Goetzel et al., "The Long-Term Impact of Johnson & Johnson's Health & Wellness Program on Employee Health Risks", Journal of Occupational Environmental Medicine vol. 44, No. 5, dated May 2002; pp. 417-424.
Goetzel et al., "The Relationship Between Modifiable Health Risks and Health Care Expenditures: An Analysis of the Multi-Employer HERO Health Risk and Cost Database", Journal of Occupational Environmental Medicine, vol. 40, No. 10; pp. 1-30.
Goetzel et al., "The Workforce Wellness Index", Journal of Occupational Environmental Medicine vol. 55, No. 3, dated Mar. 2013; pp. 272-279.
Goetzel et al., "The Predictive Validity of the HERO Scorecard in Determining Future Health Care Cost and Risk Trends", Journal of Occupational Environmental Medicine vol. 56, No. 2, dated Feb. 2014; pp. 136-144.
Kelly et al., "The Novartis Health Index: A Method for Valuing the Economic Impact of Risk Reduction in a Workforce" Journal of Occupational Environmental Medicine vol. 52, No. 5, dated May 2010; pp. 528-535.
Prochaska et al., "The Well-Being Assessment for Productivity", Journal of Occupational Environmental Medicine vol. 53, No. 7, dated Jul. 2011; pp. 735-768.
Slater et al., "Taking Steps: The Influence of a Walking Technique on Presence in Virtual Reality", ACM Transactions on Computer-Human Interaction, Sep. 1995, pp. 201-219, vol. 2 No. 3.
Sullivan, "Making the Business Case for Health and Productivity Management", Journal of Occupational Environmental Medicine vol. 46, No. 6 suppl, dated Jun. 2004; pp. S56-S61.
World Economic Forum, "The Workplace Wellness Alliance-Making the Right Investment: Employee Health and the Power of Metrics" dated Jan. 2013; pp. 1-36.
USPTO Communication for U.S. Appl. No. 13/540,262, mailed Apr. 9, 2014. (pp. 1-56).
USPTO Communication for U.S. Appl. No. 13/540,153, mailed Apr. 9, 2014. (pp. 1-50).
USPTO Communication for U.S. Appl. No. 13/540,180, mailed Apr. 9, 2014. (pp. 1-49).
USPTO Communication for U.S. Appl. No. 13/540,335, mailed Apr. 25, 2014. (pp. 1-48).
"40 Best Companies for Leaders—2014" Chief Executive, available as of Dec. 13, 2015 at the website: http://chiefexecutive.net/40-best-companies-for-leaders-2014/; pp. 1-3.
Amato, Neil, "Top 20 companies for leadership development" CGMA Magazine, Sep. 23, 2013; available as of Dec. 13, 2015 at the website: http://www.cgma.org/magazine/news/pages/20138765.aspx?TestCookiesEnabled=redirect; pp. 1-5.
Asplund, Christopher L., et al. "A central role for the lateral prefrontal cortex in goal-directed and stimulus-driven attention." Nature neuroscience 13.4 (2010): 507-512.
Asplund, Christopher L., et al. "The attentional blink reveals the probabilistic nature of discrete conscious perception." Psychological science 25.3 (2014): 824-831.
Borah, J. "Conceptual modeling—The missing link of simulation development." Proceedings of the 2002 Spring Simulation Conference. 2002. AEgis Technologies Group; pp. 1-7.
Burkus, David, "For Leaders, Looking Healthy Matters More than Looking Smart" Harvard Business Review, Jan. 2, 2015; available as of Dec. 13, 2015 at the website: https://hbr.org/2015/01/for-leaders-looking-healthy-matters-more-than-looking-smart.
Duke, Sean, "A 'smartphone' based defibrillator" Science Spin, Jan. 11, 2011: pp. 1-2.
Dux, Paul E., and René Marois. "The attentional blink: A review of data and theory." Attention, Perception, & Psychophysics 71.8 (2009): 1683-1700.
Dux, Paul E., et al. "Training improves multitasking performance by increasing the speed of information processing in human prefrontal cortex." Neuron 63.1 (2009): 127-138.
Electric double-layer capacitor Wikipedia; available at the website: http://en.wikipedia.org/wiki/electric_double-layer_capacitor as of Dec. 5, 2014; pp. 1-8.
Elliott, Stephen N., et al. "Cognitive load theory: Instruction-based research with applications for designing tests." Proceedings of the National Association of School Psychologists' Annual Convention, Boston, MA, February. vol. 24. 2009.
Fadel, Charles, et al. "Multimodal Learning Through Media: What the Research Says" Cisco Systems, Inc. (2008) pp. 1-24.
Fadjo, Cameron L., et al. "Pedagogy and Curriculum for Video Game Programming Using Scratch." Institute for Learning Technologies, Teachers College, Columbia University, New York, NY, presented at the Scratch Conference, Aug. 13, 2010; pp. 1-2.
Filmer, Hannah L., et al. "Disrupting prefrontal cortex prevents performance gains from sensory-motor training." The Journal of Neuroscience 33.47 (2013): 18654-18660.
Fougnie, Daryl, and René Marois. "What limits working memory capacity? Evidence for modality-specific sources to the simultaneous storage of visual and auditory arrays." Journal of Experimental Psychology: Learning, Memory, and Cognition 37.6 (2011): 132.
Hill, Jr., Randall W.; "How Virtual Humans Can Build Better Leaders" Harvard Business Review Jul. 25, 2014; pp. 1-4.
Horseman, Samantha, et al.; "Gamefication of Health, Safety and the Environment {HSE): An Avatarial Solution" American Society of Safety Engineers 11th Professional Development Conference & Exhibition, Bahrain, Mar. 2014;pp. 1-10.
Ivanoff, Jason, Philip Branning, and René Marois. "fMRI evidence for a dual process account of the speed-accuracy tradeoff in decision-making." PLoS one 3.7 (2008): e2635. pp. 1-14.
Jamison, Dean T., et al.; "The World Health Report 1999" World Health Organization, WHO Library Cataloguing in Publication Data, 1999; pp. 1-136.
Knikou, Maria. "The H-reflex as a probe: pathways and pitfalls." Journal of neuroscience methods 171.1 (2008): 1-12.
Lamkin, Paul; "The best VR headsets: Oculust Rift, PlayStation VR, Gear VR, HTC Vive . . . virtual reality is back baby" 10 Sep. 16, 2015; available as of Oct. 21, 2015 at the website: http://www.wearable.com/headgear/the-best-ar-and-vrheadsets;pp. 1-1.
Marois, René, and Jason Ivanoff. "Capacity limits of information processing in the brain." Trends in cognitive sciences 9.6 (2005): 296-305.
Moreno, Roxana, and Alfred Valdez. "Cognitive load and learning effects of having students organize pictures and words in multimedia environments: The role of student interactivity and feedback." Educational Technology Research and Development 53.3 (2005.
Moreno, Roxana, and Richard Mayer. "Interactive multimodal learning environments." Educational Psychology Review 19.3 (2007): 309-326.
Moreno, Roxana. "Learning in high-tech and multimedia environments." Current directions in psychological science 15.2 (2006): 63-67.
Myatt, Mike, "The #1 Reason Leadership Development Fails" Forbes, Dec. 19, 2012; available as of Dec. 13, 2015 at the website: http://www.forbes.com/sites/mikemyatt/2012/12/19/the-1-reason-leadership-development-fails/#7e53fcd834ce; pp.
Nintendo of America Inc., Wii Balance Board Operations Manual, 2008, pp. 1-10.
Nintendo of America Inc., Wii Fit Instruction Booklet, 2008, pp. 1-28.
Ovans, Andrea; "What Resilience Means, and Why it Matters" Harvard Business Review Jan. 5, 2015; pp. 1-6.

(56) References Cited

OTHER PUBLICATIONS

Qlik Technology Partners available as of Oct. 21, 2015 at the website: http://www.qlik.com/us/partners/technologypartners;pp. 1-21.
Quick, James Campbell, et al. "Executive health: Building strength, managing risks" Academy of Management Executive, May 2000, vol. 14, No. 2, pp. 33-45.
Rao, Leena; "Backed by Google Ventures and Eric Schmidt, Urban Engines Wants to Solve Urban Congestion Using Data Intelligence" available as of Oct. 2, 2015 at the website: http://www.techcrunch.com/2014/05/15/backed-by-google-entures-and-eric-schmidt-urban.
Raybourn, Elaine M., et al. "Adaptive thinking & leadership simulation game training for special forces officers." ITSEC 2005 Proceedings, Interservice/Industry Training, Simulation and Education Conference Proceedings, Nov. 2005.
Ready, Douglas A., et al.; "Are You a High Potential?" Harvard Business Review Jun. 2010; pp. 1-13.
Rimor, Rikki, Yigal Rosen, and Kefaya Naser. "Complexity of social interactions in collaborative learning: The case of online database environment." Interdisciplinary Journal of E-Learning and Learning Objects 6.1 (2010): 355-365.
Rosen, Yigal. "The effects of an animation-based on-line learning environment on transfer of knowledge and on motivation for science and technology learning." Journal of Educational Computing Research 40.4 (2009): 451-467.
Seligman, Martin E.P., "Building Resilience" Harvard Business Review from the Apr. 2011 issue; available as of Dec. 13, 2015 at the website: https://hbr.org/2011/04/building-resilience; pp. 1-15.
Simmonds, Bethany, et al. "Objectively assessed physical activity and subsequent health service use of UK adults aged 70 and over: A four to five year follow up study." PloS one 9.5 (2014): e97676.
Spisak, Brian R., et al., "A face for all seasons: Searching for context-specific leadership traits and discovering a general preference for perceived health" Frontiers in Human Neuroscience; Nov. 5, 2014; available as of Dec. 13, 2015 at the web.
Veeva Systems and Zinc Ahead Join Forces available as of Oct. 2, 2015 at the website: http://www.veeva.com; pp. 1-6.
Wang, Xiaoning. "An Empirical Study of Optimizing Cognitive Load in Multimedia Integrated English Teaching." Studies in Literature and Language 9.3 (2014): 70.
"Augmented Reality", retrieved from <http://en.wikipedia.org/wiki/Augmented_reality>, May 30, 2012. pp. 1-18.
"Biofeedback—MayoClinic.com", retrieved from <http://www.mayoclinic.com/health/biofeedback/MY01072>, May 7, 2012. (pp. 1-2).
"Cardinus Risk Management | Ergonomic & DSE Risk Assessments", retrieved from <http://www.cardinus.com/>, Sep. 12, 2012. (pp. 1-2).
"Clever toilet checks on your health", retrieved from <http://articles.cnn.com/2005-06-28/tech/spark.toilet_1_toilet-toto-bathroom?_s=PM:TECH>, Jun. 28, 2005. (pp. 1-2).
"Electroencephalography (EEG)", retrieved from <http://www.emedicinehealth.com/script/main/art.asp?articlekey-59319&pf=3&page=1>, Jun. 11, 2012. (pp. 1-4).
"Emotiv|EEG System|Electroencephalography", retrieved from <www.emotiv.com/index.asp>, Jun. 11, 2012. (pp. 1-2).
"EmotivEPOC Software Devlopment Kit", retrieved from <www.emotiv.com/store/hardware/epoc-bci-eeg/developer-neuroheadset/>, Jun. 11, 2012. (pp. 1-2).
"Kinect—Xbox.com", retrieved from <http://www.xbox.com/en-US/kinect>, Jun. 11, 2012. (pp. 1-3).
"MomToBe: The Pregnancy Assistant 3.0", retreved from <http://3d2f.com/programs/4-230-momtobe-the-pregnancy-assistant-download.shtml>, Jun. 11, 2012. (pp. 1-2).
"Office Athlete Software Prevents Common Repetitive Stress Injuries", retrieved from <http://www.officeathlete.com/>, Sep. 14, 2012. (pp. 1-2).
"OSHA Ergonomic Solutions: Computer Workstations eTool—Checklists", retrieved from <www.osha.gov/SLTC/etools/computerworkstations/checklist.html>, Jun. 11, 2012. (pp. 1-5).
"OSHA Ergonomic Solutions: Computer Workstations eTool—Good Working Positions", retrieved from <www.osha.gov/SLTC/etools/computerworkstations/positions.html>, Jun. 11, 2012. (pp. 1-2).
"OSHA Ergonomic Solutions: Computer Workstations eTool—Work Process and Recognition", retrieved from <www.osha.gov/SLTC/etools/computerworkstations/workprocess.html>, Jun. 11, 2012. (pp. 1-2).
"OSHA Ergonomic Solutions: Computer Workstations eTool—Workstation Environment", retrieved from <www.osha.gov/SLTC/etools/computerworkstations/wkstation_enviro.html>, Jun. 11, 2012. (pp. 1-3).
"OSHA Ergonomic Solutions: Computer Workstations eTool—Workstations eTool", retrieved from <www.osha.gov/SLTC/etools/computerworkstations/index.html>, Jun. 11, 2012. (p. 1).
"Philips Research—Download Pictures", retrieved from <http://www.research.philips.com/downloads/pictures/healthcare-personal.html>, May 7, 2012. (pp. 1-2).
"Philips Research Technology Backgrounder—MyHeart project", retrieved from <http://www.research.philips.com/technologies/heartcycle/myheart-gen.html>, May 7, 2012. (pp. 1-3).
"Research programs—Philips Research", retrieved from <http://www.research.philips.com/programs/index.html>, May 7, 2012. (pp. 1-2).
"RJL Systems, Products", retrieved from <http://www.rjlsystems.com/products.shtml>, May 7, 2012. (p. 1).
"SmartHeart 5E102 Heart Rate Monitor", retrieved from <http://us.oregonscientific.com/cat-Sports-and-Health-sub-Heart-Rate-Monitors-prod-SmartHeart-SE102-Heart-Rate-Monitor.html>, May 7, 2012. (pp. 1-4).
"Speedy Assessment | Chiropractic Assessment and Patient Education", retrieved from <http://speedyassessment.com/>, May 7, 2012. (pp. 1-3).
"Stress Thermometer", retrieved from <http://www.biof.com/onlinestore/stressthermometer.asp?redirect=yes>, May 7, 2012. (pp. 1-4).
"The Wellness Imperative, Creating More Effective Organizations", World Economic Forum, 2010. (pp. 1-20).
"Wireless measurement devices—Philips", retreved from <http://www.healthcare.philips.com/us_en/products/telehealth/Products/devices.wpd>, May 7, 2012. (pp. 1-2).
"WorkPace : RSI Injury Prevention Software, Stretch Break Exercise Reminder Software", retrieved from <http://www.workpace.com/>, Sep. 14, 2012. (p. 1).
"Workrave", retrieved from <http://www.workrave.org/>, Sep. 14, 2012. (p. 1).
"www.mydailyhealth.com" retrieved from the "wayback machine" (pp. 1-20).
"Pulse Oximetry" SparkFun Electronics, Oct. 7, 2005 (p. 1).
Abstract for "Psychosocial job factors and symptoms from the locomotor system—a multicausal analysis", retrieved from <http://www.ncbi.nlm.nih.gov/pubmed/1962160>, May 7, 2012. (p. 1).
Abstract for "Signal Characteristics of EMG at Different Levels of Muscle Tension", retrieved from <http://onlinelibrary.wiley.com/doi/10.1111/j.1748-1716.1976.tb10195.x/abstract>, May 7, 2012. (p. 1).
Berry, Leonard et al., "What's the Hard Return on Employee Wellness Programs?", Harvard Business Review, Dec. 2010. (pp. 1-10).
Chapman, Larry S. MPH, "Meta-evaluation of Worksite Health Promotion Economic Return Studies: 2005 Update", Jul./Aug. 2005. (pp. 1-11).
Index for "Micro-NanoMechatronics and Human Science (MHS), 2010 International Symposium Nov. 2010", retrieved from <http://ieeexplore.ieee.org/xpl/mostRecentIssue.jsp?punumber=5658189> Ma 7, 2012. (pp. 1-5).
Copending U.S. Appl. No. 13/540,028 titled "Systems, Computer Medium and Computer-Implemented Methods for Monitoring and Improving Cognitive and Emotive Health of Employees", filed Jul. 2, 2012.

(56) References Cited

OTHER PUBLICATIONS

Copending U.S. Appl. No. 13/540,067 titled "Computer Mouse System and Associated, Computer Medium and Computer-Implemented Methods for Monitoring and Improving Health and Productivity of Employees", filed Jul. 2, 2012.
Copending U.S. Appl. No. 13/540,095 titled "Chair Pad System and Associated, Computer Medium and Computer-Implemented Methods for Monitoring and Improving Health and Productivity of Employees", filed Jul. 2, 2012.
Copending U.S. Appl. No. 13/540,124 titled "Floor Mat System and Associated, Computer Medium and Computer-Implemented Methods for Monitoring and Improving Health and Productivity of Employees", filed Jul. 2, 2012.
Copending U.S. Appl. No. 13/540,153 titled "Systems, Computer Medium and Computer-Implemented Methods for Monitoring and Improving Biometric Health of Employees", filed Jul. 2, 2012.
Copending U.S. Appl. No. 13/540,180 titled "Systems, Computer Medium and Computer-Implemented Methods for Monitoring and Improving Biomechanical Health of Employees", filed Jul. 2, 2012.
Copending U.S. Appl. No. 13/540,208 titled "Systems, Computer Medium and Computer-Implemented Methods for Coaching Employees Based Upon Monitored Health Conditions Using an Avatar", filed Jul. 2, 2012.
Copending U.S. Appl. No. 13/540,262 titled "Systems, Computer Medium and Computer-Implemented Methods for Monitoring and Improving Health and Productivity of Employees", filed Jul. 2, 2012.
Copending U.S. Appl. No. 13/540,300 titled "Systems, Computer Medium and Computer-Implemented Methods for Monitoring Health of Employees Using Mobile Devices", filed Jul. 2, 2012.
Copending U.S. Appl. No. 13/540,335 titled "Systems, Computer Medium and Computer-Implemented Methods for Providing Health Information to Employees via Augmented Reality Display", filed Jul. 2, 2012.
Copending U.S. Appl. No. 13/540,374 titled "Systems, Computer Medium and Computer-Implemented Methods for Monitoring Health and Ergonomic Status of Drivers of Vehicles", filed Jul. 2, 2012.
Copending U.S. Appl. No. 14/035,717 titled "Computer Mouse System and Associated Computer Medium for Monitoring and Improving Health and Productivity of Employees", filed Sep. 24, 2013.
Copending U.S. Appl. No. 14/035,732 titled "Methods for Monitoring and Improving Health and Productivity of Employees Using a Computer Mouse System", filed Sep. 24, 2013.
Copending U.S. Appl. No. 14/043,898 titled "Systems, Computer Medium and Computer-Implemented Methods for Quantifying and Employing Impacts of Workplace Wellness Programs", filed Oct. 2, 2013.
Copending U.S. Appl. No. 14/035,670 titled "Computer Mouse for Monitoring and Improving Health and Productivity of Employees", filed Sep. 24, 2013.
Centers for Disease Control and Prevention, 2011, "Chronic diseases and health promotion", [online] Availableat: http://www.cdc.gov/chronicdisease/ overview, [Accessed Feb. 2, 2011].
USPTO Communication for U.S. Appl. No. 13/540,067, mailed Oct. 17, 2013. (pp. 1-39).
Bed-Check Co., Bed-Check Monitoring Systems, 2006.
Final Office Action for co-pending U.S. Appl. No. 13/540,067 dated Jun. 3, 2014.
Office Action for co-pending U.S. Appl. No. 13/540,095 dated May 22, 2014.
Office Action for co-pending U.S. Appl. No. 13/540,124 dated Jul. 3, 2014.
Office Action for co-pending U.S. Appl. No. 13/540,208 dated Jun. 20, 2014.
The American Heritage Dictionary of the English Language, definition of planar, 2000.
Final Office Action for co-pending U.S. Appl. No. 13/540,335 dated Nov. 6, 2014.
Collins English Dictionary, definition of mat, 2008, retrieved at www.collinsdictionary.com.
Kuriyama, Shigeru "Visualization model for a human action based on a visual perception" Measurement and Control, Japan, Journal of the Society of Instrument and Control Engineers, Dec. 10, 2006, vol. 45, No. 12, pp. 1024-1029.
Withings, The Internet connected Body Scale, retrieved with the Wayback Machine using link at www.withings.com, Jan. 11, 2010.
Final Office Action for co-pending U.S. Appl. No. 13/540,095 dated Jan. 16, 2015.
Final Office Action for co-pending U.S. Appl. No. 13/540,153 dated Jan. 23, 2015.
Final Office Action for co-pending U.S. Appl. No. 13/540,180 dated Jan. 23, 2015.
Final Office Action for co-pending U.S. Appl. No. 13/540,262 dated Jan. 22, 2015.
Office Action for co-pending U.S. Appl. No. 13/540,028 dated Mar. 5, 2015.
Office Action for co-pending U.S. Appl. No. 13/540,300 dated Feb. 12, 2015.
Health/Medical Writers eHealthcareWorld 2000. (May 1). MyDailyHealth.com Announces New Features for Enhanced Customization, Interactivity, and Incentive Management. Business Wire, 1.
Murray Hill, Well Med Team to Offer Next Generation Online Preventive Health Services. (Nov. 3). PR Newswire, 1.
"Making a Difference", World Health Organisation, Geneva: WHO, 1999, pp. 1-136.
"National health expenditure data", Centers for Medicare & Medicaid Services, available at: <http://www.cms.gov/Research-Statistics-Data-and-Systems/Statistics-Trends-and-Reports>, accessed Nov. 18, 2013, pp. 1-2.
"Piezo Electric Energy Harvester", Midé Technology Corporation, retrieved Nov. 18, 2013. pp. 1-2.
"Signal Conditioning Piezoelectric Sensors", (PDF) Texas Instruments, Application Report SLOA033A, Sep. 2000, pp. 1-6.
"The constitution of the World Health Organization", World Health Organization, WHO Chronicle, 1947, pp. 1-202.
Aldana, S., "Financial Impact of health promotion programs: a comprehensive review of the literature", American Journal of Health Promotion,155, 2001, pp. 296-320.
Aldana, S., Merrill, R., Price, K., Hardy, A., and Hager, R., "Financial impact of a comprehensive multi-site worksite health promotion program", Preventive Medicine, 40, Jul. 2004, pp. 131-137.
Alfredo Vázquez Carazo, "Novel Piezoelectric Transducers for High Voltage Measurements", Jan. 2000 , pp. 1-277.
Baiker, K., Cutler, D., Song, Z., "Worksite wellness programs can generate savings", Health Affairs 29(2), Jan. 2010, pp. 1-8.
Berry, L.L., Mirabito, A.M., Baun, W.B., "What's the Hard Return on Employee Wellness Programs?", Harvard Business Review, Dec. 2010, pp. 1-10.
Chapman, L., "Expert opinions on 'best practice' in worksite health promotion (WHP)", Jul./Aug. 2004, pp. 1-6.
Chapman, L.. "Meta-evaluation of worksite health promotion economic return studies: 2012 Update", Mar./Apr. 2012, pp. 1-13.
Edington, D. W., "Emerging research: a view from one research centre", American Journal of Health Promotion, 15(5), May/Jun. 2001, pp. 341-349.
Edington, M., Karjalainen, T., Hirschland, D., Edington, D.W., "The UAW-GM Health Promotion Program: Successful Outcomes", American Association of Occupational Health Nursing Journal.50, Jan. 2002, pp. 26-31.
Hemp, P., "Presenteeism: At Work—But Out of It", Harvard Business Review, Oct. 2004, pp. 49-58.
Horseman, S. J ., "Healthy Human Capital as a Business Strategy: The Saudi Aramco Wellness Program (SAWP)", American Society of Safety Engineers (ME Chapter), (9) Conference Proceedings. Bahrain. Feb. 2010, pp. 178-185.
Horseman, S.J., "ErgoWELL : An Integrative Strategy", SPE Paper #: SPE-152629. Society of Petroleum Engineers, MEHESSE. Paper and Workshop, Abu Dhabi, 2012, pp. 1-17.

(56) References Cited

OTHER PUBLICATIONS

Johns, G., "Presenteeism in the Workplace: A review and research agenda", Journal of Organizational Behavior, Jul. 31, 2009, pp. 519-542.
Priya, S., "Advances in Energy Harvesting Using Low Profile Piezoelectric Transducers", Materials Science & Engineering, Springer, Mar. 2007, pp. 165-182.
Riedel, J.E., Baase, C., "The effect of disease prevention & health promotion on worksite productivity: a literature review", American Journal of Health Promotion, 15:3, Jan./Feb. 2001, pp. 167-191, 243.
Roberts, R.O.,Bergstralh, E.J., Schmidt, L., Jacobsoen,S.J., "Comparison of Self Reported and Medical Record Health Care Utilization Measures", Journal of Clinical Epidemiology, 49:9, Feb. 1996, pp. 989-995.
International Search Report & Written Opinion for International Application No. PCT/US2012/045427, dated Dec. 3, 2012. (pp. 1-14).
International Search Report & Written Opinion for International Application No. PCT/US2012/045419, dated Dec. 6, 2012. (pp. 1-16).
International Search Report & Written Opinion for International Application No. PCT/US2012/045395, dated Dec. 3, 2012. (pp. 1-16).
International Search Report & Written Opinion for International Application No. PCT/US2004/045442, dated Nov. 7, 2012. (pp. 1-14).
International Search Report & Written Opinion for International Application No. PCT/US2012/045452, dated Dec. 3, 2012. (pp. 1-14).
International Search Report & Written Opinion for International Application No. PCT/US2012/045447, dated Jan. 18, 2013. (pp. 1-12).
International Search Report & Written Opinion for International Application No. PCT/US2012/045407, dated Jan. 23, 2013. (pp. 1-15).
International Search Report & Written Opinion for International Application No. PCT/US2012/045401, dated Feb. 5, 2013. (pp. 1-13).
International Search Report & Written Opinion for International Application No. PCT/US2012/045435, dated Jan. 25, 2013. (pp. 1-14).
International Search Report & Written Opinion for International Application No. PCT/US2012/045410, dated Jan. 31, 2013. (pp. 1-13).
International Search Report & Written Opinion for International Application No. PCT/US2012/045414, dated Mar. 25, 2013. (pp. 1-13).
International Preliminary Report on Patentability for International Application No. PCT/US2012/045395, dated Jan. 7, 2014. (pp. 1-12).
International Preliminary Report on Patentability for International Application No. PCT/US2012/045401, dated Jan. 7, 2014. (pp. 1-9).
International Preliminary Report on Patentability for International Application No. PCT/US2012/045407, dated Jan. 7, 2014. (pp. 1-8).
International Preliminary Report on Patentability for International Application No. PCT/US2012/045410, dated Jan. 7, 2014. (pp. 1-8).
International Preliminary Report on Patentability for International Application No. PCT/US2012/045414, dated Jan. 7, 2014. (pp. 1-8).
International Preliminary Report on Patentability for International Application No. PCT/US2012/045419, dated Jan. 7, 2014. (pp. 1-11).
International Preliminary Report on Patentability for International Application No. PCT/US2012/045427, dated Jan. 7, 2014. (pp. 1-10).
International Preliminary Report on Patentability for International Application No. PCT/US2012/045435, dated Jan. 7, 2014. (pp. 1-10).
International Preliminary Report on Patentability for International Application No. PCT/US2012/045452, dated Jan. 7, 2014. (pp. 1-9).
International Preliminary Report on Patentability for International Application No. PCT/US2012/045447, dated Jan. 7, 2014. (pp. 1-8).
International Preliminary Report on Patentability for International Application No. PCT/US2012/045442, dated Jan. 7, 2014. (pp. 1-10).
Nintendo Wii Fit, https://www.youtube.com/watch?v=-Taruqvk30E, May 11, 2008.
"Statement in accordance with the Notice from the European Patent Office dated Oct. 1, 2007 concerning business methods" Nov. 1, 2007, 1 page, XP002456414.
EPO: "Notice from the European Patent Office dated Oct. 1, 2007 concerning business methods" Official Journal EPO, vol. 30, No. 11, Nov. 1, 2007, pp. 592-593, XP007905525.
Final Office Action for co-pending U.S. Appl. No. 13/540,028 dated Jun. 10, 2015.
Final Office Action for co-pending U.S. Appl. No. 13/540,124 dated May 14, 2015.
Final Office Action for co-pending U.S. Appl. No. 13/540,208 dated May 11, 2015.
International Search Report and Written Opinion for PCT/US2014/056427 dated Apr. 22, 2015.
International Search Report and Written Opinion for PCT/US2014/069498 dated Apr. 1, 2015.
Kymissis et al. "Parasitic Power Harvesting in Shoes" Digest of Papers, Second International Symposium on Wearable Computers, Pittsburgh, PA, Oct. 19-20, 1998, pp. 132-139, XP032385438.
Office Action for co-pending Chinese Application No. 201280042796.6 dated Mar. 24, 2015.
Office Action for co-pending Chinese Application No. 201280043029.7 dated Apr. 27, 2015.
Office Action for co-pending Japanese Application No. 2014-519273 dated Apr. 7, 2015.
Office Action for co-pending U.S. Appl. No. 13/540,067 dated Apr. 21, 2015.
Copending U.S. Appl. No. 14/180,529 titled "Chair Pad System and Associated, Computer Medium and Computer-Implemented Methods for Monitoring and Improving Health and Productivity of Employees" filed Feb. 14, 2014.
Copending U.S. Appl. No. 14/180,533 titled "Chair Pad System and Associated, Computer Medium and Computer-Implemented Methods for Monitoring and Improving Health and Productivity of Employees" filed Feb. 14, 2014.
Copending U.S. Appl. No. 14/180,536 titled "Floor Mat System and Associated, Computer Medium and Computer-Implemented Methods for Monitoring and Improving Health and Productivity of Employees" filed Feb. 14, 2014.
Copending U.S. Appl. No. 14/180,471 titled "Floor Mat System and Associated, Computer Medium and Computer-Implemented Methods for Monitoring and Improving Health and Productivity of Employees" filed Feb. 14, 2014.
Copending U.S. Appl. No. 14/180,993 titled "Systems, Computer Medium and Computer-Implemented Methods for Monitoring and Improving Biometric Health of Employees" filed Feb. 14, 2014.
Copending U.S. Appl. No. 14/181,006 titled "Systems, Computer Medium and Computer-Implemented Methods for Monitoring and Improving Biomechanical Health of Employees" filed Feb. 14, 2014.
Copending U.S. Appl. No. 14/180,978 titled "Systems, Computer Medium and Computer-Implemented Methods for Monitoring and Improving Health and Productivity of Employees" filed Feb. 14, 2014.

* cited by examiner

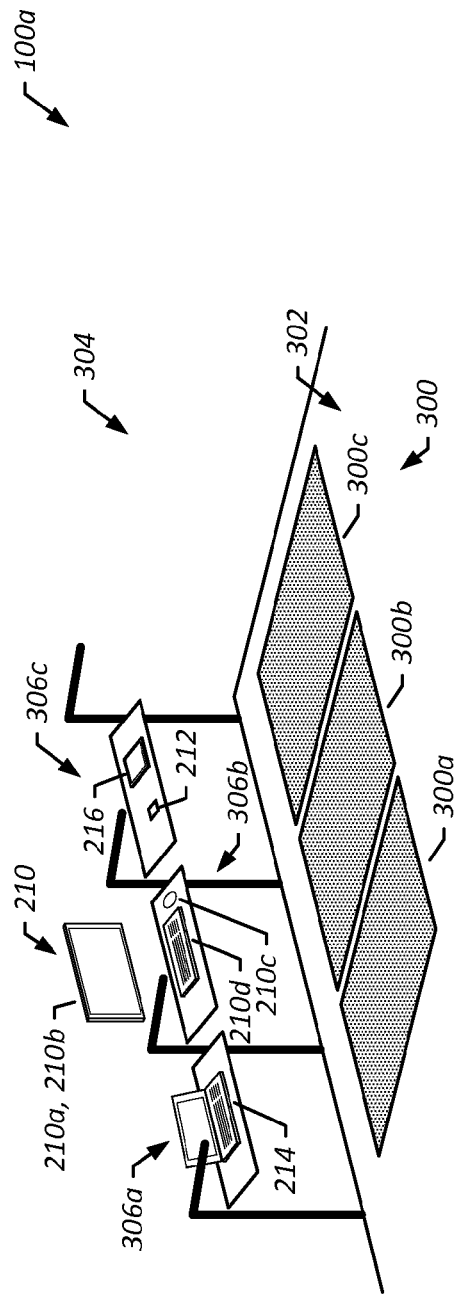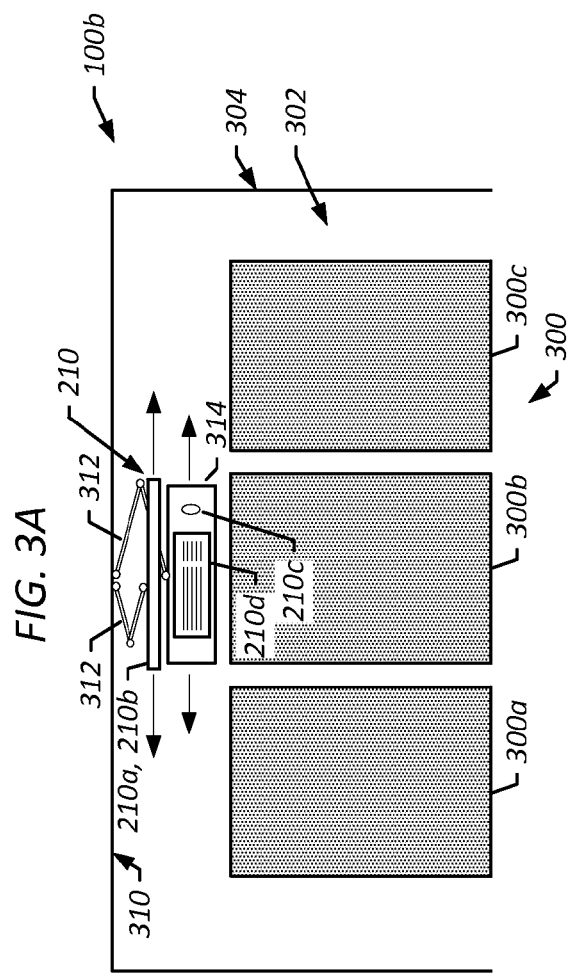
FIG. 3A
FIG. 3B

SYSTEMS, COMPUTER MEDIUM AND COMPUTER-IMPLEMENTED METHODS FOR HARVESTING HUMAN ENERGY IN THE WORKPLACE

FIELD OF INVENTION

The present invention relates generally to workplace wellness and energy conservation programs, and more particularly to systems, machines, non-transitory computer readable medium having program instructions stored thereon, and computer-implemented methods for harvesting human energy.

BACKGROUND OF THE INVENTION

Organizations (e.g., companies) are often looking for cost-effective and efficient ways to improve employee safety, health and wellness. In some instances, organizations employ workplace wellness programs to facilitate healthy lifestyles. A workplace wellness program can include, for example, organizational policies, facilities, and activities designed to encourage healthy behavior in the workplace and at home. Organizations taking part in a wellness program often provide facilities and information that support healthy lifestyles such as health literature, on-site fitness facilities, on-site medical clinics, on-site kitchens and eating areas, on-site healthy food offering and so forth. Organizations' wellness programs often involve a variety of activities, such as health fairs, health education classes, exercise classes, medical/health screenings, health coaching, weight management programs, injury prevention programs, fitness programs, and the like. In some instances, Organizations' wellness programs include organizational policies designed to facilitate a healthy work environment, such as allowing flex time for exercise, offering financial and other incentives for participation, and so forth.

It is believed that workplace wellness programs lead to a "culture of health" within a workplace that helps to prevent injury and sickness, while providing a positive impact on workforce biometric health behaviors, employee performance, and other work factors. For example, workplace wellness programs are often associated with reductions of health risks (e.g., reduced health risk associated with body mass index (BMI), blood pressure (BP), and body fat percentage) and improved work factors (e.g., improved job satisfaction, stress management, work engagement, and productivity). Moreover, workplace wellness programs can provide a positive financial benefit for organizations. For example, companies can experience reductions in medical costs due to medical risks/conditions avoided as a result of workplace wellness programs, as well as revenue increases attributable to the improved work factors (e.g., increases productivity due to improved health, reduced stress, and the like).

In addition to improving employee health, wellness and safety, organizations are often looking for ways to operate in an energy efficient manner. This can include, for example, updating their infrastructure such as replacing energy inefficient devices with newer, more efficient models. Operating in an energy efficient manner can positively impact both the organization (e.g., by reducing operating costs associated with energy consumption) and the environment (e.g., by reducing the consumption of natural resources).

Although techniques have been developed for improving employee health, wellness and safety, and for operating in an energy efficient manner, obtaining these goals typically requires organizations to engage in two distinct campaigns—one for wellness and one for energy efficiency. For example, an organization may institute a workplace wellness program that provides on-site fitness facilities, and separately institute a campaign to update inefficient areas of their infrastructure. Although these two approaches can improve aspects of employee wellness and energy efficiency separately, they still fail to fully leverage the other aspects of the workplace that can further improve employee wellness and energy efficiency.

SUMMARY OF THE INVENTION

Applicants have recognized several shortcomings of existing systems and methods for improving workplace wellness and energy efficiency in the workplace. Applicants have recognized that although existing systems and methods for improving workplace wellness can benefit employees, they often lack additional incentives to encourage employees to engage in an even healthier lifestyle. For example, although an employee may be motivated to attend an after work fitness program, they may not have any incentive to engage in exercise in their office throughout the workday. Applicants have also recognized that although existing systems and methods for improving energy efficiency in the workplace can lead to reduced power consumption, they often fail to leverage many of the available resources for improving energy efficiency. For example, although many organizations attempt to reduce power consumption by using energy efficient devices, they fail to leverage power generated by employees, such as kinetic energy generated as a result of employees' physical activities and even neural energy generated by employees' neural (or brain) activity. The capture of energy (e g, kinetic and/or neural energy) generated by humans is referred to herein as "human energy harvesting." Thus, applicants have recognized that existing systems and method often fail to provide incentives to further improve employee health and wellness, and also fail to leverage human energy harvesting in the workplace that can further improve energy efficiency. Applicants have recognized that such shortcomings have failed to be addressed by others, and have recognized that such shortcomings may be addressed by systems and methods that selectively enable and/or disable user devices based on energy harvested as a result of employee activities (e.g., employee exercise), and by systems and methods that harvest and use human kinetic and neural energy generated as a result of employee physical (e.g., kinetic) and neural (e.g., brain) activity. In some instances, these approaches can be combined to encourage employees to engage in physical activities that promote a healthy lifestyle and generate harvestable energy. In view of the foregoing, various embodiments of the present invention advantageously provide systems, machines, non-transitory computer storage medium having program instructions stored thereon, and computer-implemented methods for encouraging employees to engage in activities throughout the workday and harvesting human energy generated by the employees.

In some embodiments, provided is workplace energy harvesting system for harvesting energy from an employee. The system includes one or more electronic user devices, a human energy harvesting system, and an energy harvesting control system. The human energy harvesting system includes a kinetic energy harvesting system having one or more kinetic energy harvesting devices adapted to harvest kinetic energy generated by physical activity of the employee. The human energy harvesting system also includes a neural energy harvesting system having one or more neural energy harvesting devices adapted to harvest neural energy generated by neural activity of the employee. The energy harvesting control system is adapted to determine an amount of energy harvested and selectively enable/disable at least one of the one or more electronic user devices based at least in part on the amount of energy harvested. The amount of energy harvested can be a sum total of the kinetic energy harvested via the kinetic energy harvesting system and the neural energy harvested via the neural energy harvesting system.

In some embodiments, the kinetic energy system includes a plurality of exercise devices disposed on a floor of the employee's office such that the employee can engage a different exercise device when located at different positions in the office. In certain embodiments, each of the plurality of exercise devices includes a walking platform such that the employee can engage a different walking platform when located at different positions in the office. In some embodiments, each of the plurality of exercise devices is associated with a different set of one or more electronic user devices, and operation of a set of electronic user devices is based at least in part on an amount of energy harvested as a result use of the associated exercise device.

In certain embodiments, the energy harvesting control system is adapted to enable a set of electronic devices associated with an exercise device when an amount of energy harvested as a result of use of the exercise device satisfies an energy threshold value, and/or disable the set of electronic devices associated with the exercise device when the amount of energy harvested as a result of use of the exercise device does not satisfy the energy threshold value.

In some embodiments, selectively enabling/disabling one or more electronic user devices based at least in part on the amount of energy harvested includes determining whether the amount of energy harvested satisfies an energy threshold amount, enabling at least one of the one or more electronic user devices in response to determining that the amount of energy harvested satisfies the energy threshold, and/or disabling at least one of the one or more electronic user devices in response to determining that the amount of energy harvested does not satisfy the energy threshold amount. In certain embodiments, the energy threshold amount can be modified by the employee.

In certain embodiments, the one or more electronic user devices include a first set of one or more electronic user devices associated with a first energy threshold amount and a second set of one or more electronic user devices associated with a second energy threshold amount, and selectively enabling/disabling one or more electronic user devices based at least in part on the amount of energy harvested includes the following: determining whether the amount of energy harvested satisfies the first energy threshold amount, enabling the first set of one or more electronic user devices in response to determining that the amount of energy harvested satisfies the first energy threshold amount, and/or disabling the first set of one or more electronic user devices in response to determining that the amount of energy harvested does not satisfy the first energy threshold amount. The process further includes determining whether the amount of energy harvested satisfies the second energy threshold amount, enabling the second set of one or more electronic user devices in response to determining that the amount of energy harvested satisfies the second energy threshold amount, and/or disabling the second set of one or more electronic user devices in response to determining that the amount of energy harvested does not satisfy the second energy threshold amount.

In some embodiments, the kinetic energy system includes a piezoelectric transducer adapted to harvest power generated by a hip-flexor of the employee and/or a fitness/exercise device. In certain embodiments, the neural energy system includes a neural headset including one or more neural energy transducers adapted to be disposed about a head of the employee.

In certain embodiments, the system includes an energy storage device, and the energy harvesting control system is adapted to provide for storing at least a portion of the energy harvested in the energy storage device when the energy harvested is not required to power an electronic user device, and to at least partially power an electronic user device using energy stored by the energy storage device. In some embodiments, the system includes a connection to an electrical power grid, and the energy harvesting control system is adapted to at least partially power an electronic user device using energy provided via the electrical power grid. In certain embodiments, the system includes an energy storage device and an alternative energy source, and the energy harvesting control system is adapted to at least partially power an electronic user device simultaneously using at least two of the following: energy stored by the energy storage device, energy currently being provided by the human energy harvest system, and energy provided by the alternative power source.

In some embodiments, the system includes an energy harvest user interface that is adapted to display metrics for energy harvested and status information for the one or more electronic user devices, and a coaching avatar.

In certain embodiments, provided is a system for harvesting human energy from an employee. The system includes a human energy harvesting system and an energy harvesting control system. The human energy harvesting system includes one or more kinetic energy harvesting devices adapted to harvest kinetic energy generated by physical activity of the employee. The one or more kinetic energy devices include a plurality of walking platforms disposed on a floor of the employee's office such that the employee can engage a different walking platform when located at different positions in the office. A walking platform is adapted to harvest kinetic energy generated by the employee when walking on the walking platform. The energy harvesting control system is adapted to determine an amount of energy harvested via human energy harvesting system (e.g., the amount of energy harvested includes energy harvested via the plurality of walking platforms) and to selectively enable/disable one or more electronic user devices based at least in part on the amount of energy harvested.

In some embodiments, the system includes one or more neural energy harvesting devices adapted to harvest neural energy generated by neural activity of the employee. In certain embodiments, selectively enabling/disabling one or more electronic user devices based at least in part on the amount of energy harvested includes determining whether the amount of energy harvested satisfies an energy threshold amount, enabling at least one of the one or more electronic user devices in response to determining that the amount of energy harvested satisfies the energy threshold amount, and/or disabling at least one of the one or more electronic user devices in response to determining that the amount of energy harvested does not satisfy the energy threshold amount.

In certain embodiments, the energy harvesting control system is adapted to determine whether an amount of energy generated by use of a walking platform satisfies a walking platform energy threshold amount, enable at least one of one or more electronic user devices associated with the walking platform in response to determining that the amount of energy generated by use of the walking platform satisfies the walking platform energy threshold amount, and/or disable at least one of one or more electronic user devices associated with the walking platform in response to determining that the amount of energy generated by use of the walking platform does not satisfy the walking platform energy threshold amount.

In certain embodiments, provided is a method for harvesting human energy from an employee. The method includes determining an amount of energy harvested and selectively enabling/disabling one or more electronic user devices based at least in part on the amount of energy harvested. The amount of energy harvested includes an amount of kinetic energy harvested and an amount of neural energy harvested. The kinetic energy is harvested by a kinetic energy system including one or more kinetic energy harvesting devices that harvest kinetic energy generated by physical activity of an employee. The neural energy is harvested by a neural energy system including one or more neural energy harvesting devices that harvest neural energy generated by neural activity of the employee.

In some embodiments, the kinetic energy system includes a plurality of exercise devices disposed on a floor the employee's office such that the employee can engage a different exercise device when located at different positions in the office. In certain embodiments, selectively enabling/disabling one or more electronic user devices based at least in part on the amount of energy harvested includes determining whether the amount of energy harvested satisfies an energy threshold amount, and enabling at least one of the one or more electronic user devices in response to determining that the amount of energy harvested satisfies the energy threshold amount and/or disabling at least one of the one or more electronic user devices in response to determining that the amount of energy harvested does not satisfy the energy threshold amount.

Accordingly, as described herein, embodiments of the system, computer program instructions and associated computer-implemented methods provide for harvesting human energy.

BRIEF DESCRIPTION OF THE DRAWINGS

FIGS. 3A and 3B illustrate office environments including an office energy harvesting system in accordance with one or more embodiments of the present invention.

Figure 1:
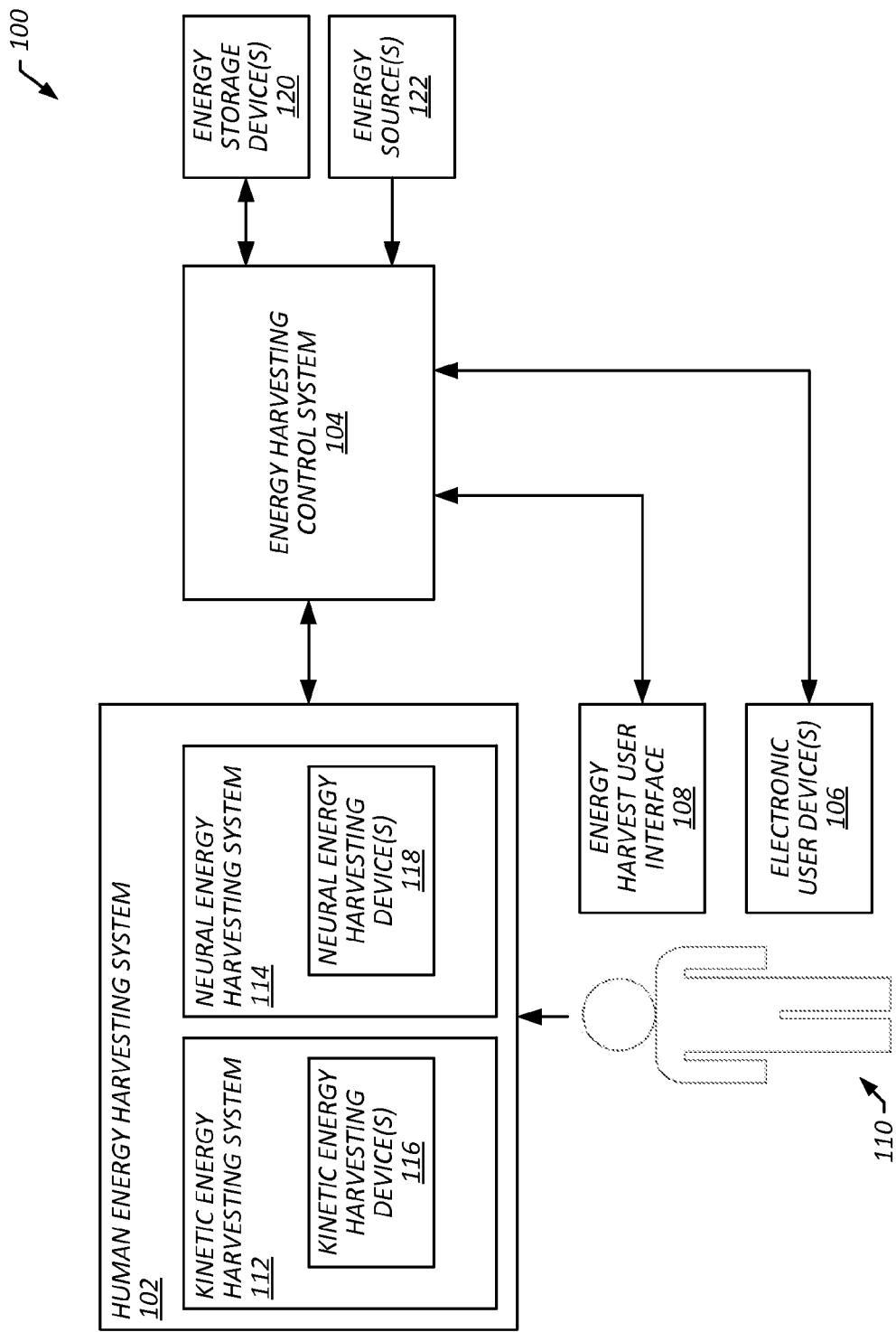
FIG. 1 is a block diagram that illustrates a workplace energy harvesting system in accordance with one or more embodiments of the present invention.

While the invention is susceptible to various modifications and alternative forms, specific embodiments of the invention are shown by way of example in the drawings and will be described in detail herein. It should be understood, however, that the drawings and detailed description thereof are not intended to limit the invention to the particular form disclosed, but to the contrary, are intended to cover all modifications, equivalents, and alternatives falling within the spirit and scope of the present invention as defined by the appended claims.

DETAILED DESCRIPTION

Provided herein are embodiments that include workplace energy harvesting systems and methods that harvest human energy and encourage employees to engage in activities while working Harvesting human energy may include capturing energy that is expended by a person such that it can be repurposed for another use. For example, harvesting energy generated by a user walking on a treadmill can include capturing the energy generated by the resulting movement of the belt as the user walks in place on the belt, and using that energy to power another device, such as a computer, and/or storing that energy in a battery for later use. In some embodiments, a workplace energy harvesting system includes electronic user devices (e.g., a computer, a mobile phone, a tablet computer, a laptop computer and/or the like), a human energy harvesting system, an energy harvesting control system and/or an energy harvest user interface.

In some embodiments, a human energy harvesting system includes a kinetic energy harvesting system and/or a neural energy harvesting system. A kinetic energy harvesting system may include, for example, one or more kinetic energy harvesting devices that can harvest kinetic energy generated as a result of physical movement, such as movement induced by a person (e.g., an employee) during exercise or other physical activity. A kinetic energy harvesting device may include, for example, a treadmill, an elliptical machine, a stair climber, a stationary bicycle, and/or other fitness/exercise equipment. A kinetic energy device may include, for example, a piezoelectric transducer that can harvest kinetic energy generated as a result of movement. In some embodiments, a piezoelectric transducer may be positioned to capture energy expended by movement when a person engages in physical activity. For example, a piezoelectric transducer can be positioned at a person's hip-flexor and/or under their foot to capture energy expended while they walk or engage in other physical activity.

A neural energy harvesting system may include, for example, one or more neural energy harvesting devices, such as one or more a neural energy transducers, that can be used to harvest neural (or brain) energy. A neural energy harvesting device may include, for example, a neural headset having one or more neural energy transducers that can be disposed about a person's head (e.g., worn on an employee's head). In some embodiments, a neural headset provides for the positioning of one or more neural energy transducers about a person's scalp for use in harvesting neural energy generated by the person's brain activity throughout the workday.

In some embodiments, an energy harvesting control system manages energy harvesting by selectively enabling/disabling one or more electronic user devices, and/or managing the distribution of harvested energy to one or more devices of the system. For example, an energy harvesting control system may selectively enable/disable at least one of the one or more electronic user devices based at least in part on an amount of energy harvested. As described herein, an "amount of energy" may be expressed as a rate (e.g., 25 Watts (W)), a quantity (e.g., 25 Watt-hours), or variants thereof (e.g., an average of 25 Watts per minute). In some embodiments, an energy harvesting control system enables one or more electronic devices when an amount of energy harvested satisfies an energy threshold amount, and/or disable one or more electronic devices when an amount of energy harvested does not satisfy an energy threshold amount. In the context of enabling/disabling a device, an energy harvesting control system may, for example, disable an employee's tablet computer when it is determined that the employee's use of a treadmill results in the harvest of less than a threshold amount of power and enable the tablet computer when it is determined that the employee's use of the treadmill results in the harvest of at least a threshold amount of power. In some embodiments, enabling/disabling a device includes enabling/disabling one or more features thereof. For example, an energy harvesting control system may disable a text-messaging feature of an employee's mobile phone when it is determined that the employee's use of the treadmill results in the harvest of less than a threshold amount of power and enable the text-messaging feature when it is determined that the employee's use of a treadmill results in the harvest of at least threshold amount of power. Such conditioned based device enablement/disablement provides incentives that encourage employees to participate in an active lifestyle. For example, an employee may be more likely to walk on a treadmill for an extended period if they know that the additional activity provides access to devices and features that may not otherwise be available.

In some embodiments, a kinetic energy harvesting system includes a plurality of walking platforms (e.g., treadmills) disposed on the floor of an employee's office or similar work space. Each of the walking platforms can be disposed in different locations about the workspace such that the employee can move to different areas of the office while continuing to engage in a walking exercise. For example, three walking platforms can be disposed adjacent one another such that an employee can move from one walking station to the next while completing work duties at each of the respective stations. In such an arrangement, an employee may not be required to suspend their physical activity simply because they needed to move to a different location within the office. In some embodiments, each of the walking platforms are associated with a different set of one or more electronic user devices and enabling/disabling of at least one of the electronic user devices is based at least in part on the energy harvested as a result of the employee walking on the associated walking platform. For example, a computer system disposed adjacent a first walking platform may be enabled when the employee is walking on the first walking platform, and a tablet computer provided adjacent a second walking platform may be enabled when the employee is walking on the second walking platform.

In some embodiments, harvested power is used to power one or more electronic user devices. For example, an energy harvesting control system may direct harvested power to an employee's cellular phone to maintain its charge. In some embodiments, harvested power is stored for later use. For example, an energy harvesting control system may direct harvested power to an energy storage device, such as a battery. The stored energy may be used at a later time to power (or at least partially power) one or more electronic user devices. In some embodiments, an alternative power source, such as an electrical power grid, is used to power one or more electronic user devices. For example, energy harvesting control system may power one or more electronic user devices using the electrical power grid when harvesting energy is not possible (or practical), and/or when the energy currently being harvested and/or the stored energy is not sufficient to power an electronic user device. In some embodiments, different energy sources are used in conjunction with one another (e.g., simultaneously) to provide the power needed to operate one or more electronic devices. For example, if an electronic user device requires 20W of power to operate, energy harvesting control system may provide the device with 10W of power from the currently harvested energy (e.g., energy that currently being generated by an employee's walking on a walking platform), 5W of power from a battery (e.g., energy that was generated by an employee's walking on the walking platform earlier in the day and stored in the battery) and 5W of power drawn from the electrical power grid. In this instance, for example, although harvested power is being supplemented by power from the electrical power grid, the power consumption from the electrical power grid is still reduced by approximately 75%.

In some embodiments, an energy user interface is provided to communicate information regarding the harvesting of energy and/or the status of various electronic user devices. An energy user interface may display, for example, a listing of energy harvest metrics, such as a current energy harvest rate (e.g., with a breakdown of the energy sources), a current energy usage rate, an indication of the quantity of energy harvested that day, an average energy harvested, an indication of the year-to-date energy harvested, and/or the like. An energy user interface may also display, for example, the status of various electronic user devices that are enabled/disabled, threshold energy harvest amounts associated with the various devices, coaching information, and/or the like. Such an interface can be updated in real-time to provide a mechanism to encourage employees to engage in physical activity.

Although certain embodiments are described herein with regard to a work environment, such as an office, embodiments of the invention can be employed in any variety of applications. For example, the described systems and methods can be employed in a home environment for use by a homeowner, in a gym environment for use by gym patrons, and/or the like. Moreover, although certain embodiments are described in the context of a particular type of apparatus for the purpose of illustration, other embodiments may include a variety of other apparatus. For example, although a walking platform (e.g., a treadmill) is used in exemplary embodiments for the purpose of illustration, a variety of exercise equipment can be used, such as an elliptical machine, a stair-stepper, a stationary bike, and/or the like.

FIG. 1 is a block diagram that illustrates a workplace energy harvesting system ("system") 100 in accordance with one or more embodiments of the present invention. In the illustrated embodiment, system 100 includes a human energy harvesting system 102, an energy harvesting control system 104, one or more electronic user devices ("electronic user device(s)") 106, and an energy harvest user interface 108. In the illustrated embodiment, system 100 also includes one or more energy storage devices ("energy storage device(s)") 120, and one or more alternative energy/power sources ("energy source(s)") 122.

In some embodiments, human energy harvesting system 102 includes a kinetic energy harvesting system 112 and/or a neural energy harvesting system 114. Kinetic energy harvesting system 112 may be employed to harvest kinetic energy generated by a person (e.g., an employee) 110. Neural energy harvesting system 114 may be employed to harvest neural energy generated by person 110. In some embodiments, kinetic energy harvesting system 112 includes one or more kinetic energy harvesting devices ("kinetic energy harvesting device(s)") 116. A kinetic energy harvesting device 116 may harvest kinetic energy generated as a result of movement, such as movement by person 110 during exercise or other physical activity. A kinetic energy harvesting device 116 may include, for example, a treadmill, an elliptical machine, a stair climber, a stationary bike, and/or other fitness/exercise equipment. In some embodiments, a kinetic energy harvesting device is disposed on a walking surface. For example, a kinetic energy harvesting device 116 may include one or more walking tiles or similar walking surfaces that harvest energy from footsteps of one or more persons. Such walking tiles may include those manufactured by Pavegen Systems, headquartered in London, England. In some embodiments, a kinetic energy device 116 includes a piezoelectric transducer that harvest kinetic energy generated as a result of movement. In some embodiments, a piezoelectric transducer may be positioned to harvest energy generated by movement when a person engages in physical activity. For example, a piezoelectric transducer is positioned at a hip-flexor of person 110 to capture kinetic energy generated at the hip-flexor when person 110 walks or engage in other physical activity. A piezoelectric transducer may be positioned under a foot of person 110 to capture kinetic energy generated when person 110 walks or engage in other physical activity. For example, a piezoelectric transducer may be positioned in the sole of a shoe worn by person 110 to capture kinetic energy generated when person 110 walks or engage in other physical activity. Such a shoe may include the technology described in "Parasitic Power Harvesting in Shoes" by Kymissis et al., MIT Media Laboratory E15-410, August 1998.

In some embodiments, neural energy harvesting system 114 includes one or more neural energy harvesting devices ("neural energy harvesting device(s)") 118. A neural energy harvesting device 118 may include, for example, one or more a neural energy transducers, that harvest neural (or brain) energy generated by person 110. In some embodiments, a neural energy harvesting device 118 includes a neural headset having one or more neural energy transducers that can be disposed about the head of person 110. In some embodiments, the headset provides for the positioning of the one or more neural energy transducers about the scalp of person 110 for use in harvesting neural (or brain) energy generated by brain activity of person 110 throughout the workday. Such a headset may include an Emotiv EPOC headset (or a similar headset) manufactured by Emotiv, of San Francisco, Calif., or a MindWave headset (or a similar headset) manufactured by NeuroSky, headquartered in San Jose, Calif.

In some embodiments, an energy harvesting control system 104 manages energy harvesting by selectively enabling/disabling one or more electronic user devices 106, and/or managing the distribution of harvested energy to one or more devices of system 100. For example, energy harvesting control system 104 may selectively enable/disable at least one of the one or more electronic user devices 106 based at least in part on an amount of energy harvested (e.g., kinetic and/or neural energy harvested). Kinetic energy harvested may include energy harvested via kinetic energy harvesting system 112. Neural energy may include energy harvested via neural energy harvesting system 114. In some embodiments, energy harvesting control system 104 enables (e.g., powers-on or unlocks) one or more of electronic devices 106 when an amount of energy harvested satisfies an energy threshold amount, and/or disables (e.g., powers-off or locks) one or more of electronic devices 106 when an amount of energy harvested does not satisfy an energy threshold amount. In the context of enabling/disabling a device, energy harvesting control system 104 may, for example, enable an electronic device 106 (e.g., a tablet computer) when it is determined that an amount of energy harvested satisfies an energy threshold amount associated with the electronic device 106 and/or disable the same electronic device 106 when it is determined that an amount of energy harvested does not satisfy the energy threshold amount associated with the electronic device 106. In some embodiments, enabling/disabling a device includes enabling/disabling one or more features thereof. For example, energy harvesting control system 104 may enable one or more features of an electronic device 106 (e.g., a text-messaging feature of a mobile phone) when it is determined that an amount of energy harvested satisfies an energy threshold amount associated with the feature and/or disable the one or more features of the electronic device 106 when it is determined that an amount of energy harvested does not satisfy the energy threshold amount associated with the feature. Such conditioned based device enablement/disablement may provide incentives that encourage person 110 to participate in an active lifestyle. For example, person 110 may be more likely to walk on a treadmill for an extended period if he/she knows that that the additional activity provides access to devices and features that may not otherwise be available. A device or feature may be considered to be "unlocked" when the device or feature is available for use. A device or feature may be considered to be "locked" when the device or feature is not available for use. In some instances, a disabled device may be powered-on and locked such that, although the device is powered-on and operating, certain functionality or features of the device are not available for use. In some embodiments, a controller provides for controlling a device by regulating power supplied to the device. For example, a controller may disable a device by turning off power to the device and/or enable a device by turning on power to the device. In some embodiments, a controller controls functionality of a device via a control signal that is indicative of a desired state of the device. For example, a controller may provide for disabling functionality of a device by supplying a disable control signal to the device. The device may interpret the disable signal and disable functionality (e.g., power-off the device or disable one or more features of the device) in accordance with the disable signal. Similarly, a controller may provide for enabling functionality of a device by supplying an enable control signal to the device. The device may interpret the enable signal and enable functionality (e.g., power-on the device or enable one or more features of the device) in accordance with the enable signal.

A controller may include any suitable controlling device, such as a controller integrated within a device (e.g., an integrated device controller), the user's computer, a network server, and/or the like.

In some embodiments, harvested energy is used to power one or more of electronic user devices 106. For example, energy harvesting control system 104 may direct power from the harvested energy to one more of user devices 106 to enable or otherwise power their operation (e.g., direct harvested power to an employee's cellular phone to maintain its charge). In some embodiments, harvested energy is stored for later use. For example, energy harvesting control system 104 may direct power from harvested energy to one or more energy storage devices 120. In some embodiments, an energy storage device includes a battery or similar energy storage device. In some embodiments, particularly where the amount of energy harvested is small (e.g., in a micro-harvesting application), an energy storage device can include a highly efficient solid-state battery, such as a CymbetEnerchip solid-state battery manufactured by Cymbet Corporation headquartered in Elk River, Minn., or a super-capacitor such as a HB series PowerStor super-capacitor manufactured by Cooper Bussmann headquartered in Cleveland, Ohio. In some embodiments, the stored energy can be used at a later time to power (or at least partially power) one or more of electronic user devices 106 or other devices. In some embodiments, one or more alternative power sources, such as an electrical power grid can be used to power one or more of electronic user devices 106. For example, energy harvesting control system 104 may provide for powering one or more of electronic user devices 106 using energy source(s) 122 when harvesting energy is not possible (or practical), and/or when the currently harvested energy and/or the energy stored in energy storage device(s) 120 is not sufficient to power one or more of electronic user devices 106. In some embodiments, different energy sources are used in conjunction with one another (e.g., simultaneously) to provide the power needed to enable/operate one or more of electronic device(s) 106. For example, if an electronic user device 106 requires 20W to operate, energy harvesting control system 104 may provide the device with a combination 10W of power from the currently harvested energy (e g, kinetic and/or neural energy that is currently being generated by and harvested from person 110), 5W of power from one or more energy storage device(s) 120 (e g, kinetic and/or neural energy that was previously generated by person 110 and stored in energy storage devices 120) and 5W of power drawn from energy source(s) 122 (e.g., energy from an electrical power grid). In this instance, for example, although harvested power is being supplemented by an alternative energy source, the power consumption from the alternative power source is reduced by approximately 75% (e.g., 5W is being drawn from the power grid as opposed to the 20W required to operate the device).

In some embodiments, energy harvest user interface 108 communicates information regarding the harvesting of energy and/or the status of various electronic user devices 106. Energy harvest user interface 108 may display, for example, a listing of energy harvest metrics, such as a current energy harvest rate (e.g., with a breakdown of the energy sources), a current energy usage rate, an indication of the quantity of energy harvested that day, an average energy harvested, an indication of the year-to-date energy harvested, and/or the like. Energy harvest user interface 108 may also display, for example, the status of various electronic user devices 106 that are enabled/disabled, associated threshold powers needed to enable various devices, coaching information, and/or the like. Such an interface can be updated in real-time (e.g., within seconds or a few minutes). Energy harvest user interface 108 may encourage employees to engage in physical activity.

Figure 2A:
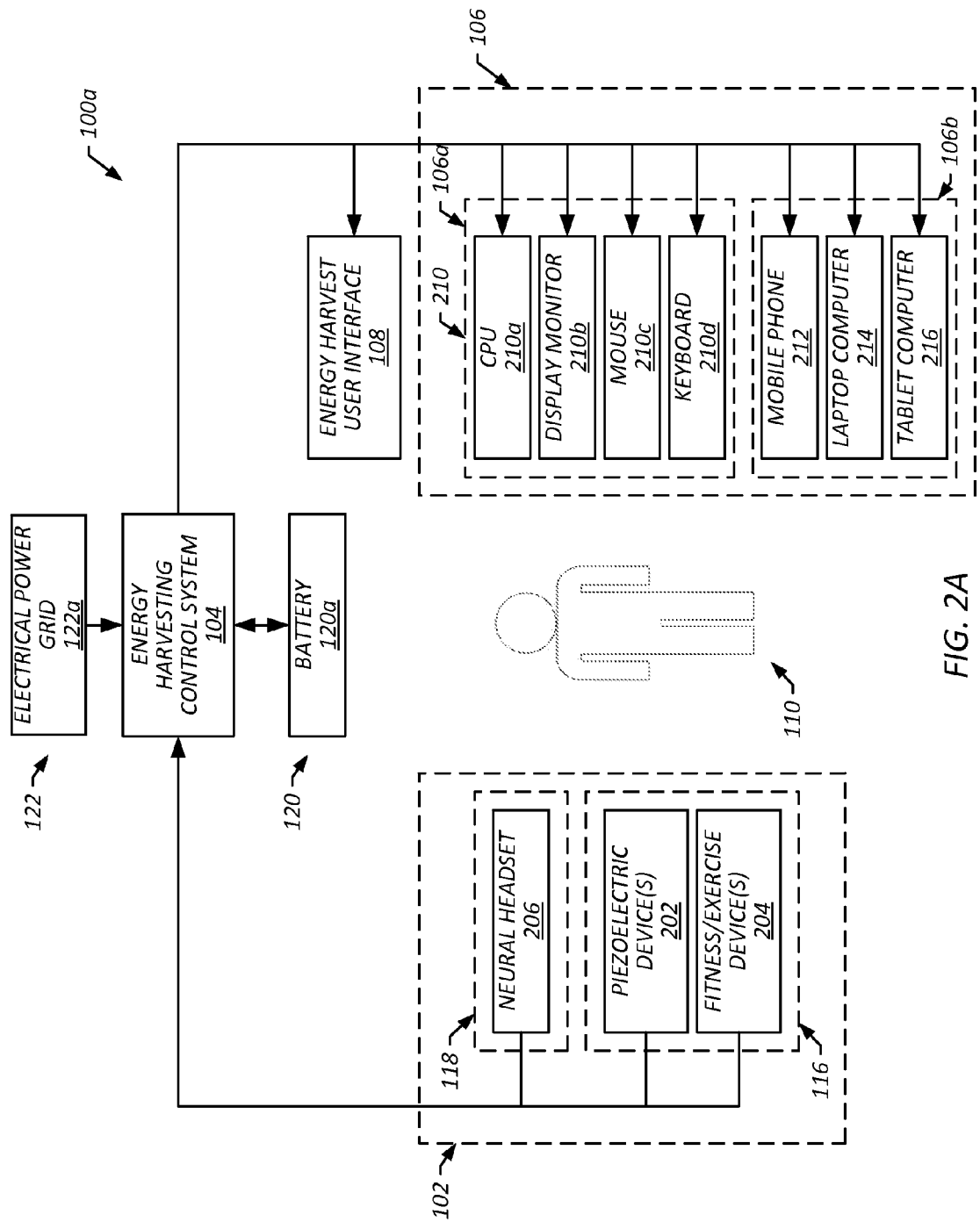
FIG. 2A is a block diagram that illustrates an office energy harvesting system in accordance with one or more embodiments of the present invention.

FIG. 2A is a block diagram that illustrates an office energy harvesting system ("office system") 100a in accordance with one or more embodiments of the present invention. In the illustrated embodiment, system 100a includes human energy harvesting system 102, energy harvesting control system 104, electronic user device(s) 106, energy harvest user interface 108, energy storage device(s) 120, and energy source(s) 122.

In the illustrated embodiment, energy source(s) 122 includes an electrical power grid 122a. Energy harvesting control system 104 may be electrically coupled to power grid 122a (e.g., plugged into a wall-outlet of an office of employee 110 that connects to power grid 122a). During operation, energy harvesting control system 104 may use power provided by electrical power grid 122a to fully (or at least partially) power one or more of electronic user devices 106.

In the illustrated embodiment, energy storages device(s) 120 include one or more batteries 120a. Energy harvesting control system 104 may be electrically coupled to one or more batteries 120a. During operation, energy harvesting control system 104 may use power provided by one or more batteries 120a to fully (or at least partially) power one or more of electronic user devices 106.

In the illustrated embodiment, kinetic energy harvesting device(s) 116 of human energy harvesting system 102 include one or more piezoelectric devices ("piezoelectric device(s)") 202 and one or more fitness/exercise devices ("fitness/exercise device(s)") 204. In some embodiments, at least one of the one or more piezoelectric devices 202 are positioned at the hip-flexor and/or under the foot of employee 110 to capture energy expended when employee 110 walks or engages in other physical activity. For example, a first piezoelectric device may be positioned at the hip-flexor of employee 110 and/or a second piezoelectric device may be positioned in the heel of a shoe worn by employee 110.

In some embodiments, one or more exercise/fitness devices 204 include an exercise/fitness device that requires a user to expend kinetic energy during use. For example, an exercise/fitness device 204 may include, for example, a treadmill (e.g., a walking platform), an elliptical machine, a stair climber, a stationary bike, and/or the like. Embodiments that employ multiple exercise/fitness devices 204 are described in more detail herein with regard to at least FIGS. 3A and 3B.

In the illustrated embodiment, neural energy harvesting device(s) 118 of human energy harvesting system 102 includes a neural headset 206. Neural headset 206 may include one or more neural energy transducers physically coupled to a frame that can be worn about the head/scalp of employee 110. The frame of neural headset 206 may provide for the positioning of one or more neural energy transducers about a scalp of employee 110 for use in harvesting neural energy generated by brain activity of employee 110.

In the illustrated embodiment, one or more electronic user devices 106 include one or more local electronic user devices ("local electronic user device(s)") 106a and/or one or more mobile electronic user devices ("mobile electronic user device(s)") 106b. In some embodiments, local electronic user devices 106a include electronic devices that are typically found in an office environment, such as workstation/desk-top-computer 210. Workstation/computer 210 may include for example, a central processing unit (CPU) 210*a*, a display monitor 210*b*, a mouse 210*c*, and/or a keyboard 210*d*. Although local electronic user devices may be removed from an office environment with some effort, they are typically associated with a fixed position, such as within an office, and are not moved frequently (e.g., they are not moved on a daily basis and/or are not typically carried with an individual on a daily basis). In some embodiments, mobile electronic devices include portable electronic devices that are typically carried with an individual. Mobile electronic device(s) 106*b* may include, for example, a mobile phone (e.g., a cellular/smart phone) 212, a laptop computer 214, a tablet computer 216, and/or the like.

Figure 2B:
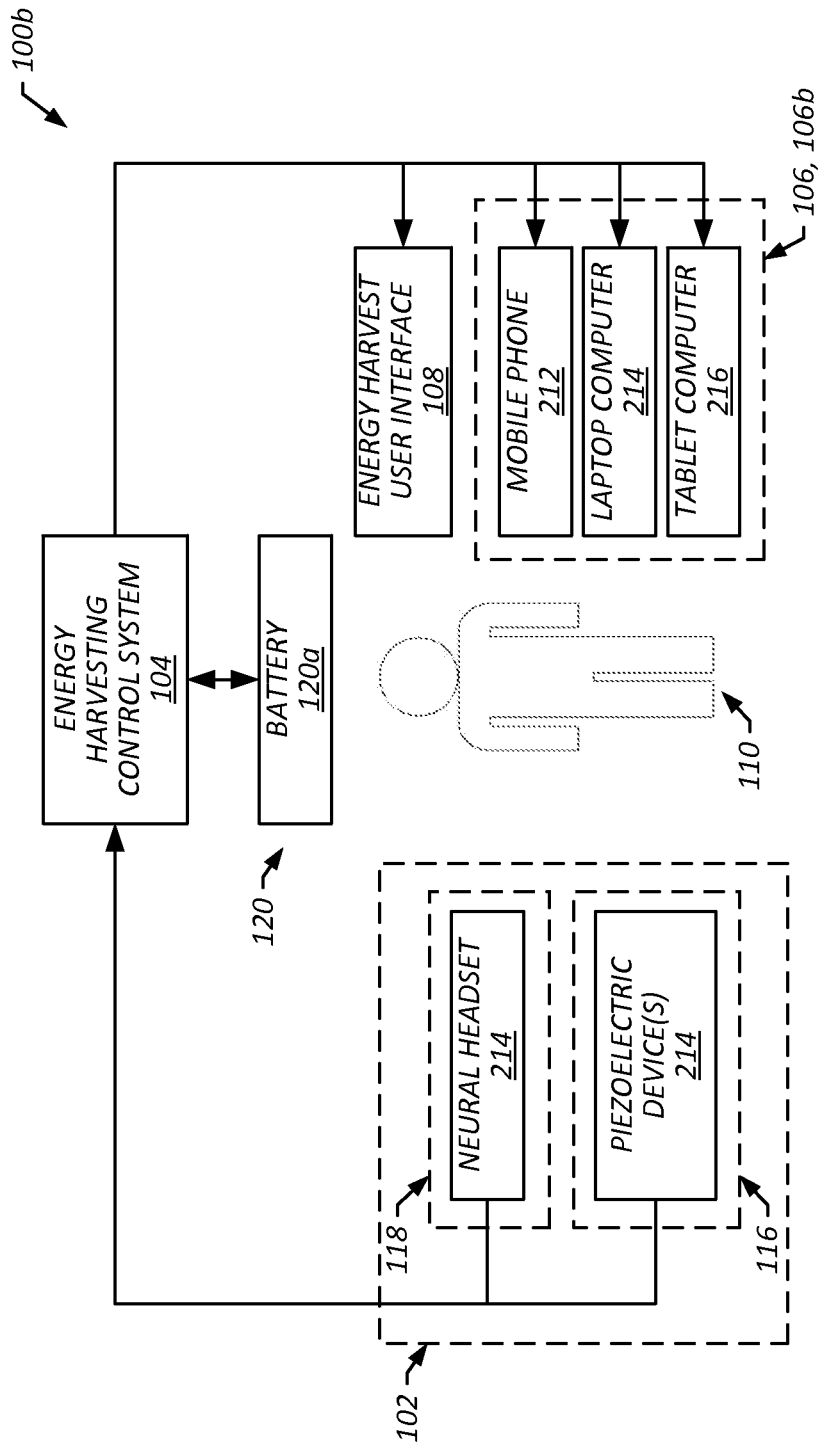
FIG. 2B is a block diagram that illustrates a mobile energy harvesting system in accordance with one or more embodiments of the present invention.

FIG. 2B is a block diagram that illustrates a mobile energy harvesting system ("mobile system") 100*b* in accordance with one or more embodiments of the present invention. In the illustrated embodiment, mobile system 100*b* includes human energy harvesting system 102, energy harvesting control system 104, electronic device(s) 106, energy harvest user interface 108, and an energy storage device(s) 120.

In some embodiments, mobile system 100*b* does not include exercise/fitness devices 204 as the system is intended to be mobile and, thus, inclusion of traditional stationary exercise/fitness (e.g., a treadmill, an elliptical machine, a stair climber, stationary bike and/or the like) may not be practical as it could limit the mobility of the system. Of course, in some embodiments, an optional connection from energy harvesting control system 104 to exercise/fitness devices 204 (e.g., a treadmill, an elliptical machine, a stair climber, stationary bike, and/or the like) may be provided so that mobile system 100*b* can incorporate such devices if desired.

In some embodiments, mobile system 100*b* does not include local electronic user devices 106*a* as the system is intended to be mobile and, thus, inclusion of local electronic user devices (e.g., a workstation/desktop computer) may not be practical as it could limit the mobility of the system. Of course, in some embodiments, an optional connection from energy harvesting control system 206 to local electronic user devices 106*a* (e.g., a workstation/desktop computer) may be provided so that mobile system 100*b* can incorporate such devices if desired.

In some embodiments, mobile system 100*b* does not include an alternative power source 122 as the system is intended to be mobile and, thus, inclusion of an alternative power source (e.g., including a fixed connection to an electrical grid) may not be practical as it could limit the mobility of the system. Of course, in some embodiments, an optional connection to an alternative power source 122 may be provided so that mobile system 100*b* can be provided with additional power if needed. For example, if a sufficient amount of energy is not being harvested to power devices 106 and/or battery 120*a* is depleted, employee 110 may be able to simply plug energy harvesting control system 104 into a power outlet connected to the electrical power grid to obtain power for devices 106 and/or to charge battery 120*a*. Such a configuration may enable mobile system 100*b* to be substantially self-sufficient—requiring minimal physical tethering to other external/non-mobile devices.

FIG. 3A illustrates an office system 100*a* in accordance with one or more embodiments of the present invention. In the illustrated embodiment, three fitness/exercise devices 300 (300*a*, 300*b* and 300*c*) are provided on a floor 302 of an employee's office 304. In some embodiments, fitness/exercise devices 300*a*, 300*b* and 300*c* each include a walking platform (e.g., a treadmill including a belt that circulates about one or more cylindrical drums). In such an embodiment, placing the walking platforms in different locations about office 304 allows employee 110 to move freely to different areas of office 304 to complete work duties while walking Thus, for example, employee 110 may not be required to suspend physical activity simply because they needed to move to a different location within office 304.

In some embodiments, a first set of one or more electronic user devices 306*a* (e.g., laptop computer 214) is associated with a first fitness/exercise device 300*a*, a second set of one or more electronic user devices 306*b* (e.g., workstation/desktop-computer 210) is associated with a second fitness/exercise device 300*b*, and a third set of one or more electronic user devices 306*c* (e.g., mobile phone 212 and tablet computer 216) is associated with a third fitness/exercise device 300*c*. In some embodiments, enabling/disabling of at least one of the electronic user devices is based at least in part on the energy harvested as a result of the employee using the associated fitness/exercise device. For example, a first set of one or more electronic user devices 306*a* (e.g., laptop computer 214) associated with the first walking platform 300*a* may be enabled when employee 110 is walking on the first walking platform, a second set of one or more electronic user devices 306*b* (e.g., workstation/desktop-computer 210—including CPU 210*a*, display monitor 210*b*, mouse 210*c* and keyboard 210*d*) associated with the second walking platform 300*b* may be enabled when employee 110 is walking on the second walking platform, and a third set of one or more electronic user devices 306*c* (e.g., mobile phone 212 and tablet computer 216) associated with the third walking platform 300*c* may be enabled when employee 110 is walking on the third walking platform. As a further example, the sets of one or more electronic user devices 306*a*, 306*b* and 306*c* may be disabled when employee 110 is not walking on the corresponding first, second, or third walking platform.

In some embodiments, enabling sets of devices associated with a given platform is based at least in part on whether or not a threshold amount of power is being harvested as a result of employee 110 using the associated walking platform. For example, the first set of one or more electronic user devices 306*a* (e.g., laptop computer 214) associated with the first walking platform 300*a* may be enabled for use if an energy threshold amount is 25W, and 35W is being harvested as a result of the employee 110 walking on the first walking platform 300*a*. In contrast, the first set of one or more electronic user devices 306*a* (e.g., laptop computer 214) associated with the first walking platform 300*a* may be disabled if only 15W (less than the energy threshold amount of 25W) is being harvested as a result of the employee 110 walking on the first walking platform 300*a*.

Although the above embodiment describes three fitness/exercise devices 300 aligned in parallel with one another, other embodiment may include any number of devices arranged in any suitable fashion. For example, two, four five, six, or more walking platforms can be provided about office 304 in any variety of configurations. Although the above embodiment describes each of fitness/exercise devices 300*a*, 300*b* and 300*c* being a walking platform for the purpose of illustration, in some embodiments, different types of fitness/exercise device can be used. For example, fitness/exercise devices 300 can include any combination of a treadmill, an elliptical machine, a stair climber, stationary bike or other fitness/exercise equipment. That is, for example, device 300*a* may be a walking platform, device 300*b* may be an elliptical machine, and device 300*c* may be a stair climber. Such varied types of exercise equipment may allow employee 110 to engage in different types of exercise while completing his/her work duties.

FIG. 3B illustrates an office system 100b in accordance with one or more embodiments of the present invention. In the illustrated embodiment, three fitness/exercise devices 300 (300a, 300b and 300c) are provided on a floor 302 of an employee's office 304. In some embodiments, each of fitness/exercise devices 300 includes a different type of fitness/exercise device. For example, first fitness/exercise device 300a may include a walking platform, second fitness/exercise device 300b may include an elliptical machine, and third fitness/exercise device 300c may include a stair-climber machine. Providing different types of fitness/exercise devices 300 may allow employee 110 to engage in different types of exercise while completing their work duties from within office 304. For example, employee may work via computer 210 (in a first position) from 10:00 am to 10:30 am while walking on walking platform (fitness/exercise device 300a), then work via computer 210 (in a second position) from 10:31 am to 11:00 am while exercising on the elliptical machine (fitness/exercise device 300b), and then work via computer 210 (in a third position) from 11:01 am to 11:30 am while exercising on the stair climber (fitness/exercise device 300c).

In some embodiments, movement between fitness/exercise devices is facilitated by adjustable mounting hardware that allows electronic user devices to be repositioned for use as the user moves from one location to another. For example, display monitor 210b and a tray 314 that supports keyboard 210d and mouse 210c may be coupled to a wall 310 of office 304 via one or more articulating arms 312 that allows the devices to be repositioned for use while employee 110 is using the different exercise equipment. For example, when employee 110 is using the walking platform (a first fitness/exercise device 300a) arms 312 may enable display monitor 210b and tray 314 (supporting keyboard 210d and mouse 210c) to be moved to the left into a first position (as illustrated by the arrows pointing to the left) such that they are positioned directly in front of the walking platform. Similarly, when employee 110 is using the stair climber (a third fitness/exercise device 300c) arms 312 may enable display monitor 210b and tray 314 (supporting keyboard 210d and mouse 210c) to be moved to the right into a third position (as illustrated by the arrows pointing to the right) such that they are positioned directly in front of the stair climber.

Figure 4:
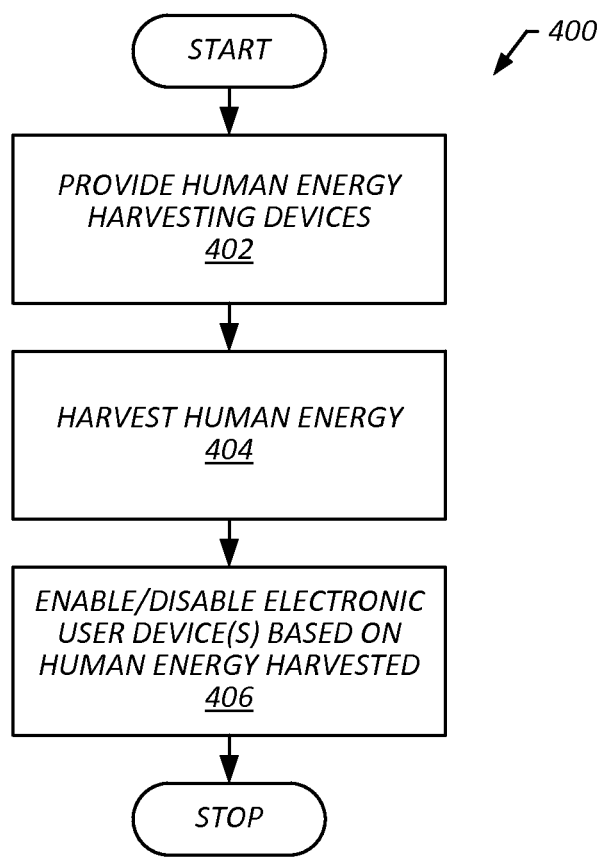
FIG. 4 is a flowchart that illustrates a method for enabling/disabling devices based on human energy harvested in accordance with one or more embodiments of the present invention.

FIG. 4 is a flowchart that illustrates a method 400 for enabling/disabling electronic user devices based on human energy harvested in accordance with one more embodiments of the present invention. Method 400 generally includes providing human energy harvesting device(s) (block 402), harvesting human energy (block 404) and enabling/disabling electronic user device(s) based on human energy harvested (block 406).

In some embodiments, providing human energy harvesting device(s) (block 402) includes providing one or more kinetic energy harvesting devices 116 and/or providing one or more neural energy harvesting devices 118. For example, in the context of workplace human energy harvesting, providing human energy harvesting device(s) may include providing a neural headset 206 to be worn about the head/scalp of employee 110 to capture neural energy generated by the employee's brain activity throughout the workday, providing one or more piezoelectric devices 202 that are worn by employee 110 to capture energy expended by the person during exercise or other physical activity throughout the workday, and/or providing one or more fitness/exercise devices 204 for capturing energy produced by employee 110 during exercise or other physical activity using the fitness/exercise device(s) 204.

In some embodiments, harvesting human energy (block 404) includes harvesting energy that is generated by an employee 110 throughout the workday using the provided human energy harvesting devices. For example, harvesting human energy may include kinetic energy harvesting system 112 harvesting kinetic energy expended by employee 110 throughout the workday (e.g., via exercise or some other form of physical activity) via one or more kinetic energy harvesting devices 116. Further, harvesting human energy may include neural energy harvesting system 114 harvesting neural energy generated by brain activity of employee 110 throughout the workday via one or more neural energy harvesting devices 118. Thus, in some embodiments, harvesting human energy includes human energy harvesting system 102 harvesting kinetic and/or neural energy that is generated by an employee 110 throughout the workday using one or more kinetic and neural energy harvesting devices 116 and 118. Kinetic energy harvested may include energy harvested via kinetic energy harvesting system 112 and the one or more associated kinetic energy devices 116. Neural energy harvested may include energy harvested via neural energy harvesting system 114 and the one or more associated kinetic energy devices 118.

In some embodiments, harvesting human energy (block 404) includes providing harvested human energy to an energy harvesting control system. For example, energy harvested (e g, kinetic and neural energy harvested) by human energy harvesting system 102 may be provided to energy harvesting control system 104. In some embodiments, energy harvesting control system 104 manages the distribution and routing of the harvested energy to devices within system 100.

In some embodiments, enabling/disabling electronic user devices based on human energy harvested (block 406) includes selectively enabling/disabling at least one of the one or more electronic user devices based at least in part on an amount of energy harvested. In some embodiments, energy harvesting control system 104 enables one or more of electronic devices 106 when an amount of energy harvested satisfies an energy threshold amount associated with the one or more of electronic devices 106, and/or disables one or more of electronic devices 106 when an amount of energy harvested does not satisfy an energy threshold amount associated with the one or more of electronic devices 106. In the context of enabling/disabling a device, energy harvesting control system 104 may, for example, enable an electronic device 106 (e.g., a tablet computer) when it is determined that an amount of energy harvested satisfies an energy threshold amount associated with the electronic device 106 and/or disable the same electronic device 106 when it is determined that an amount of energy harvested does not satisfy the energy threshold amount associated with the electronic device 106. In some embodiments, enabling/disabling a device includes enabling/disabling one or more features thereof. For example, energy harvesting control system 104 may enable one or more features of an electronic device 106 (e.g., a text-messaging feature of a mobile phone) when it is determined that an amount of energy harvested satisfies an energy threshold amount associated with the feature and/or disable the one or more features when it is determined that an amount of energy harvested does not satisfy the energy threshold amount associated with the feature.

Figure 5A:
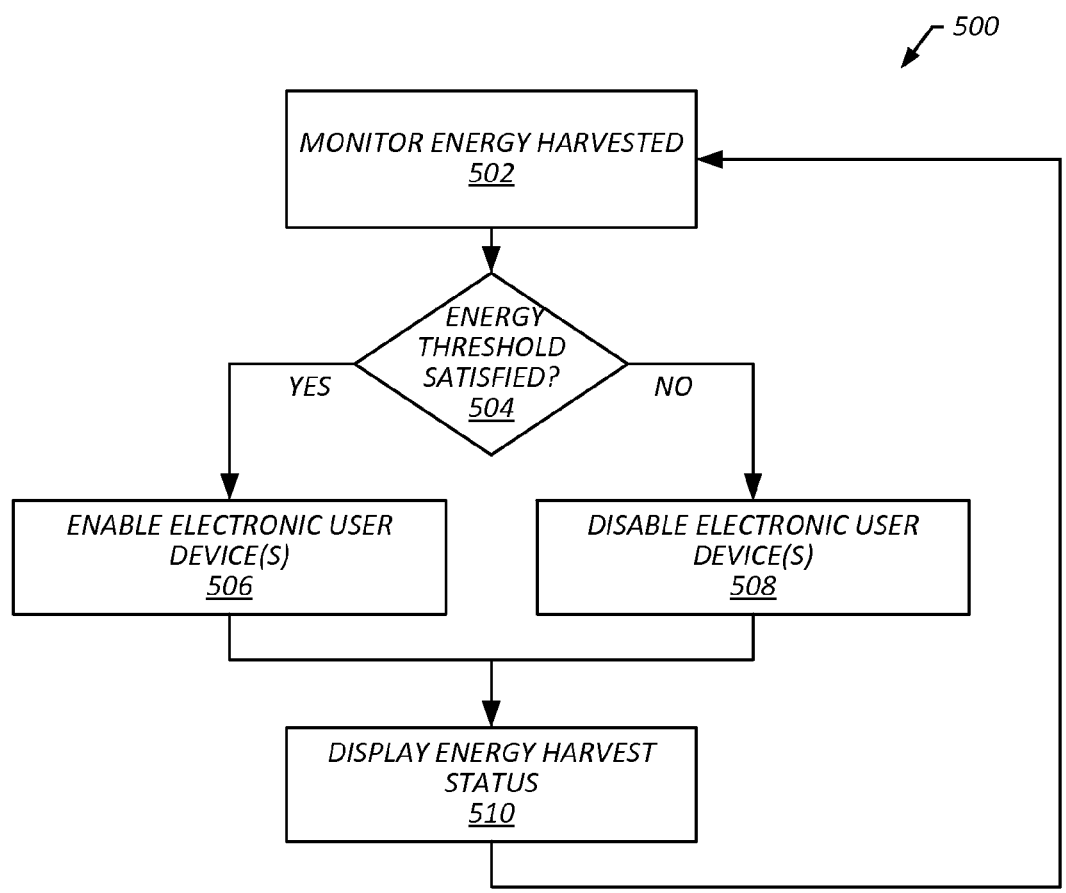
FIGS. 5A and 5B are flowcharts that illustrate methods for enabling/disabling devices based on human energy harvested in accordance with one or more embodiments of the present invention.
Figure 5B:
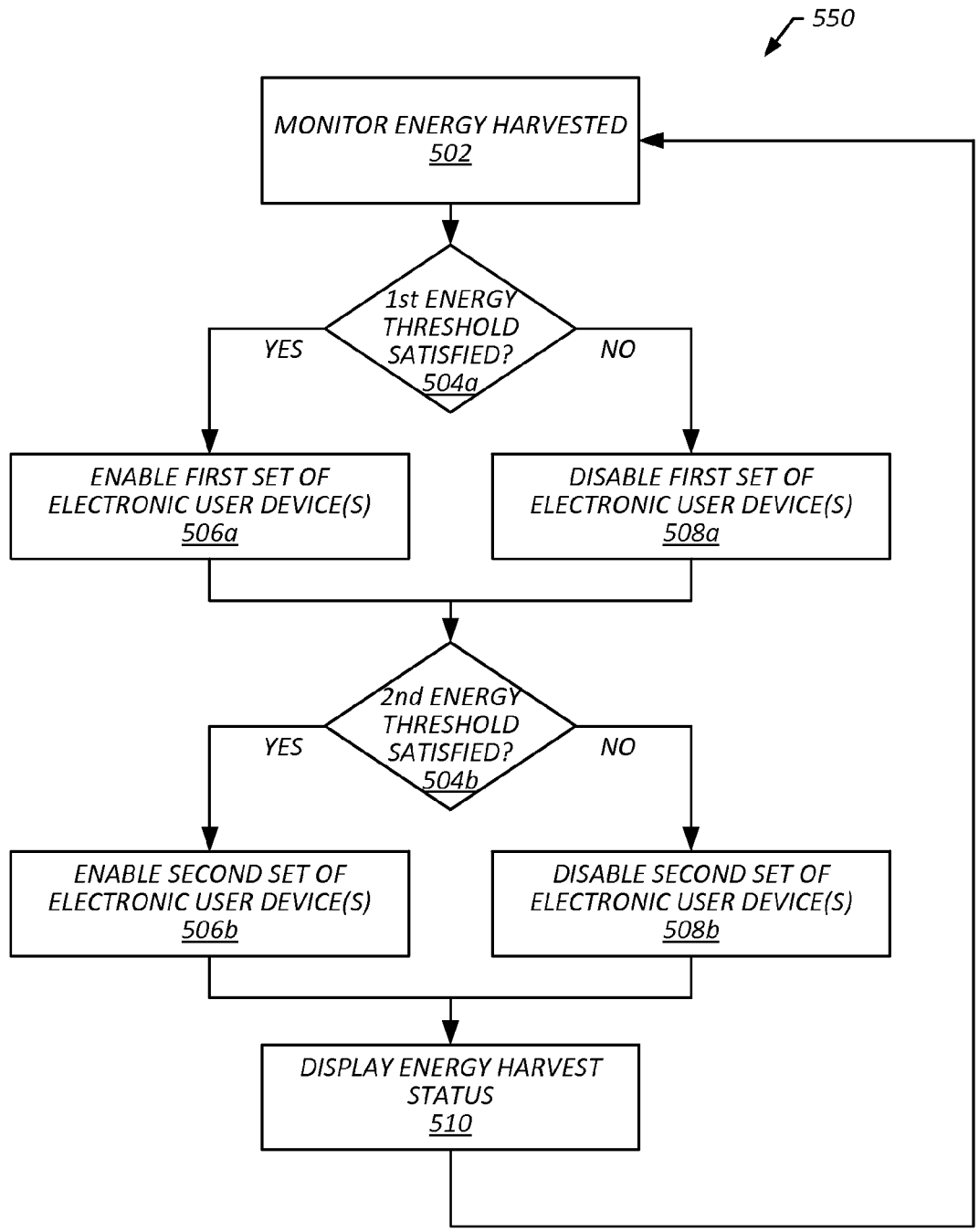

FIGS. 5A and 5B are flowcharts that illustrate methods 500 and 550 for enabling/disabling devices based on human energy harvested in accordance with one or more embodiments of the present invention. Method 500 generally includes monitoring energy harvested via a human energy harvesting system (block 502), determining whether the energy harvested satisfies an energy threshold (block 504), enabling one or more electronic user devices if the energy generated/harvested satisfies the energy threshold (block 506) and/or disabling one or more electronic user devices if the energy harvested does not satisfy the energy threshold (block 508), and displaying an energy harvest status (block 510).

In some embodiments, monitoring energy harvested via a human energy harvesting system (block 502) includes monitoring an amount of energy harvested by human energy harvesting system 102. An "amount of energy" may be expressed as a rate (e.g., 25 Watts), a quantity (e.g., 25 Watt-hours), or variants thereof (e.g., an average of 25 Watts per minute). In some embodiments, monitoring an amount of energy harvested by human energy harvesting system 102 includes energy harvesting control system 104 determining an amount of energy harvested from person 110 by human energy harvesting system 102. The energy harvested may include a sum of the kinetic energy and/or neural energy harvested.

In some embodiments, determining an amount of energy harvested from person 110 by human energy harvesting system 102 includes determining an amount of energy that is harvested for use by an electronic device and/or stored for use at a later time. For example, if user generates energy at a rate of 20W, with 15W being harvested and used to power a computer 210 and 5W being harvested and stored in energy storage device 120, it may be determined that 20W of energy is being harvested from person 110. In some embodiments, determining an amount of energy harvested from person 110 by human energy harvesting system 102 includes determining an amount of energy that is harvested and actually used, e.g., used by an electronic device or stored for use at a later time. For example, if user generates energy at a rate of 20W, with 15W being harvested and used to power a computer 210 and 0W being stored (e.g., in a system that does not include an energy storage device 120), it may be determined that 15W of energy is being harvested from person 110. In some embodiments, determining an amount of energy harvested from person 110 by human energy harvesting system 102 includes determining an amount of energy that is harvested regardless of whether or not it is actually used to power an electronic device or stored for use at a later time. For example, if user 110 generates energy at a rate of 20W and the system does not store or use that power, it can be determined that 20W of energy is being harvested from person 110. Such a determination may be useful, for example, in a system where it is possible to determine that a user is generating energy, but the infrastructure of the system does not support using the energy generated (e.g., to power an electronic user device and/or storing the energy for later use).

In some embodiments, a kinetic energy harvesting device 116 and/or human energy harvesting system 102 provides an indication of the energy generated by person 110 to energy harvesting control system 104. In such an embodiment, kinetic energy harvesting devices 116 and/or human energy harvesting system 102 may not transfer the energy generated by person 110 to harvesting control system 104. For example, a kinetic energy harvesting device 116, such as a treadmill, may measure the energy generated by person 110 walking on the treadmill, determine that the energy generated is 20W and forward a signal indicative of the 20W of energy generated to human energy harvesting system 102. Human energy harvesting system 102 may, then, forward a signal to energy harvesting control system 104 that is indicative of the 20W of energy generated. Energy harvesting control system 104 may, then, add the 20W to the amount of energy harvested. For example, if 1W is being harvested via neural energy harvesting system, 10W is being harvested via a piezoelectric energy harvesting device 202 and/or other fitness/exercise equipment 204, then energy harvesting control system 104 may determine that the total energy harvested is 31W (31W=20W+1W+10W), despite the fact that the 20W is not being used or stored. That is, an amount of energy harvested may represent a total energy generated by person 110. Such an embodiment may encourage a person to engage in physical exercise regardless of whether or not the energy generated is actually used to power an electronic device or stored for later use.

In some embodiments, determining whether the energy harvested satisfies an energy threshold (block 504) includes energy harvesting control system 104 determining whether the amount of energy harvested from person 110 (determined at block 502) is greater than or equal to a predetermined energy threshold for one or more electronic user devices. For example, if an energy threshold value is set to 15W for a set of one or more electronic user device 106 and it is determined that 20W is being harvested, energy harvesting control system 104 may determine that the energy harvested satisfies the energy threshold for the set of one or more electronic user device 106. In contrast, if an energy threshold value is set to 25W for a set of one or more electronic user device 106 and it is determined that 20W is being harvested, energy harvesting control system 104 may determine that the energy harvested does not satisfy the energy threshold for the set of one or more electronic user device 106.

In some embodiments, enabling electronic user device(s) (block 506) includes energy harvesting control system 104 enabling the one or more electronic user devices associated with the energy threshold value. For example, if computer 210 is associated with an energy threshold value of 15W, energy harvesting control system 104 may enable computer system 210 in response to determining that 20W of energy is currently being harvested from person 110. In some embodiments, enabling an electronic user device includes powering-on the electronic user device. For example, enabling computer 210 may include simply powering-on computer system 210. In some embodiments, enabling an electronic user device includes enabling one or more features of the electronic user device. For example, enabling the texting feature of mobile phone 212 may include unlocking the texting feature of mobile phone 212 so that the texting feature can be used by person 110.

In some embodiments, disabling electronic user device(s) (block 508) includes energy harvesting control system 104 disabling the one or more electronic user devices associated with the energy threshold value. For example, if computer 210 is associated with an energy threshold value of 25W, energy harvesting control system 104 may disable computer system 210 in response to determining that 20W of energy is currently being harvested from person 110. In some embodiments, disabling an electronic user device includes powering-off the electronic user device. For example, disabling computer 210 may include powering-off computer system 210. In some embodiments, disabling an electronic user device includes disabling one or more features of the electronic user device. For example, disabling the texting feature of mobile phone 212 may include locking the texting feature of mobile phone 212 so that the texting feature cannot be used by person 110.

Figure 6:
FIG. 6 illustrates display of an energy harvest status content page in accordance with one or more embodiments of the present invention.

In some embodiments, displaying an energy harvest status (block 510) includes harvesting control system 104 providing for the display information regarding the generation/harvesting of energy and/or the status of various electronic user devices. For example, energy harvesting control system 104 may serve an energy harvest status content page for display via energy harvest user interface 108. FIG. 6 illustrates display of an energy harvest status content page 600 in accordance with one or more embodiments of the present invention. Energy harvest status content page 600 may include a listing of energy harvest metrics 602. Energy harvest metrics 602 may include, for example, a current energy harvest rate (e.g., with a breakdown of the energy sources), a current energy usage rate, an indication of the quantity of energy harvested that day, an average energy harvested, an indication of the year-to-date energy harvested, and/or the like. Energy harvest status content page 600 may include device information 604. Device information 604 may include, for example, the status of various electronic user devices (e.g., enabled/disabled) and the threshold energy harvest amounts associated with the various devices, and/or the like. In some embodiments, energy harvest amounts are user selectable (e.g., as indicated by the editable fields for entering the energy harvest amounts for the mobile phone, the tablet and the texting feature), or fixed (e.g., as indicated by the lack of an editable field for the computer and the laptop threshold powers). In some embodiments, energy harvest status content page 600 includes coaching information 606. Coaching information 606 may include, for example, an animated coaching avatar 606a and/or written coaching instructions 606b that are intended to encourage and guide an employee to reach their health and wellness goals. For example, in an effort to get the person 110 to give just a bit more effort, avatar 606a may speak and/or written coaching instructions 606b may recite, "You just need to produce 5 more watts to activate your tablet . . . walk a little faster!". Such coaching can help increase the physical activity of person 110 and increase the amount of harvested power. In some embodiments, energy harvest status content page 600 can be updated in real-time (e.g., within seconds or a few minutes).

In some embodiments, the same energy threshold value may be associated with a plurality of different electronic user devices and/or features thereof. For example, if an energy threshold value is set to 15W for all of electronic devices 106, then all of electronic user devices 106 may be enabled if it is determined that 20W is currently being harvested, and, in contrast, all of electronic devices 106 may be disabled if it is determined that only 10W is currently being harvested.

In some embodiments, different electronic user devices and/or features are associated with different energy threshold values. For example, computer 210 may be associated with an energy threshold value of 0W (e.g., it is always enabled), laptop computer 214 may be associated with an energy threshold value of 15W, mobile phone 212 may be associated with an energy threshold value of 20W, and tablet computer 216 and the texting feature of mobile phone 212 may be associated with an energy threshold value of 50W. Thus, for example, if it determined that 5W of energy is currently being harvested, energy harvesting control system 104 may enable computer 210 and disable laptop computer 214, mobile phone 212, tablet computer 216 and the texting feature of mobile phone 212. As a further example, if energy harvesting control system 104 determines that 25W of energy is currently being harvested, energy harvesting control system 104 may enable computer 210, laptop computer 214 and mobile phone 212, and disable tablet computer 216 and the texting feature of mobile phone 212. As yet another example, if energy harvesting control system 104 determines that 55W of energy is currently being harvested, energy harvesting control system 104 may enable all of the electronic user devices 106 and the associated features (e.g., enable computer 210, laptop computer 214, mobile phone 212, tablet computer 216 and the texting feature of mobile phone 212).

In an embodiment in which different sets of devices are associated with different energy threshold values, similar techniques to those described in FIG. 5A may be used (e.g., the techniques described with regard to determining whether energy generated/harvested satisfies an energy threshold (block 504), enabling an electronic user device (block 506), and disabling an electronic user device (block 508) may be repeated for each of the different the different energy threshold values). FIG. 5B is a flowchart that illustrates a method 550 for enabling/disabling devices based on human energy harvested when different energy threshold values are associated with different sets of electronic user devices and/or features thereof. Method 550 operates in the same manner as that of method 500 with the exception of a separate series of steps for determining whether the different energy threshold values are satisfied (e.g., at block 504a and 504b) and providing distinct steps for enabling/disabling the sets of one or more devices associated with the respective energy thresholds (e.g., at blocks 506a/508a and 506b/508b). For example, if computer 210 is associated with a first energy threshold value of 0W and laptop computer 214 and mobile phone 212 are associated with a second energy threshold value of 15W, and energy harvesting control system 104 determines that 5W of energy is currently being harvested at block 502, energy harvesting control system 104 may determine that the first energy threshold of 0W is satisfied at block 504a, and enable computer 210 at block 506a. Energy harvesting control system 104 may determine that the second energy threshold of 15W is not satisfied (block 504b), and disable laptop computer 214 and mobile phone 212 at block 508b. Although two energy thresholds are provided for the purpose of illustration, any number of thresholds may be employed. For example, a similar method including assessment and enabling/disabling of devices based on four energy thresholds may be provided to provide for the above descried embodiment in which computer 210 is associated with a first energy threshold value of 0W (meaning it is always active), laptop computer 214 may be associated with a second energy threshold value of 15W, mobile phone 212 is associated with a third energy threshold value of 20W, and tablet computer 216 and the texting feature of mobile phone 212 are associated with a fourth energy threshold value of 50W.

Figure 7:
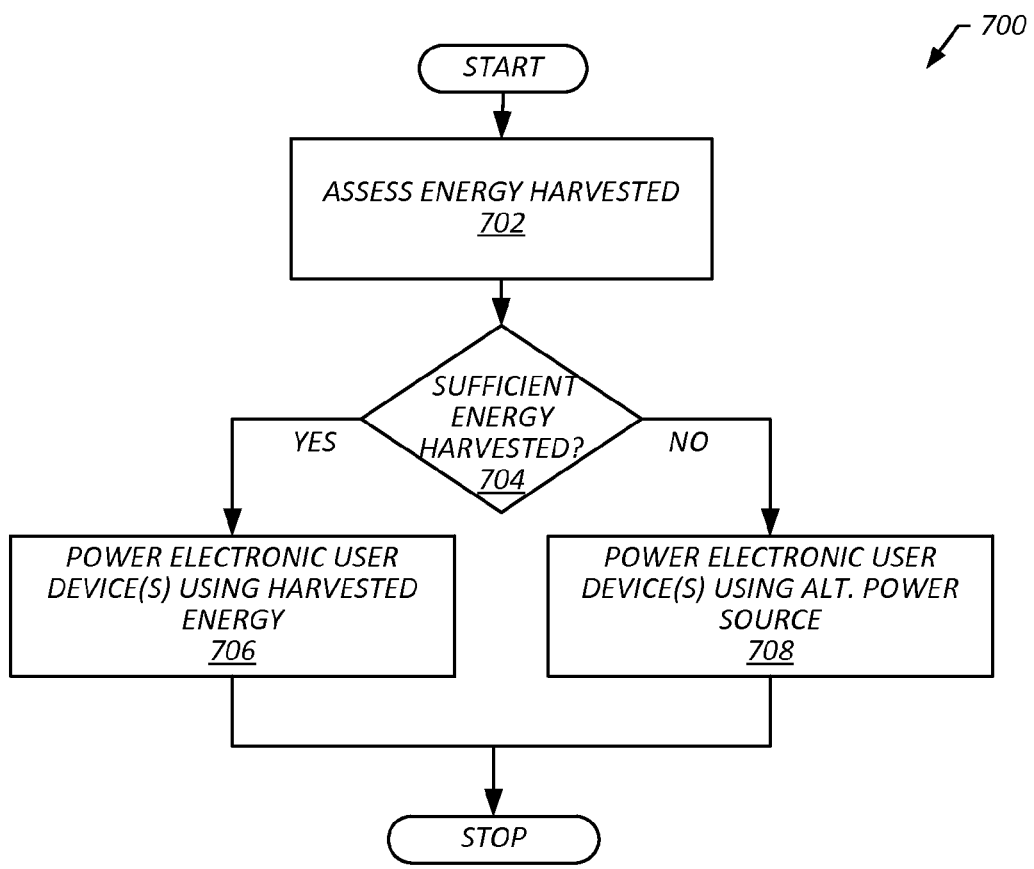
FIG. 7 is a flowchart that illustrates a method for powering devices in accordance with one or more embodiments of the present invention.

In some embodiments, enabling an electronic user device includes providing power to the device from a variety of sources. For example, energy harvesting control system 104 may power one or more electronic user devices using an alternative power source (e.g., using power from the electrical power grid) when harvesting energy is not possible (or practical), or when the currently harvested energy and/or the stored energy is not sufficient to power the one or more electronic user devices. FIG. 7 is a flowchart that illustrates a method 700 for powering devices in accordance with one or more embodiments of the present invention. Method 700 generally includes assessing the energy harvested (block 702), determining whether the energy harvested is sufficient to power one or more electronic user devices (block 704), and if it is determined that the energy harvested is sufficient to power one or more electronic user devices, powering the one or more electronic user devices using the harvested energy, and if it is determined that the energy harvested is not sufficient to power the one or more electronic user devices, powering the one or more electronic user devices using an alternative power source (block 708).

In some embodiments, assessing the energy harvested (block 702) includes determining an amount of energy currently being harvested for use. In some embodiments, determining an amount of energy currently being harvested for use includes energy harvesting control system 104 determining a total amount of energy harvested (e.g., including kinetic and neural energy currently being harvested) that can be used for powering one or more of electronic user devices 106. For example, if 1W of neural energy is currently being harvested via neural energy harvesting system 114 and 20W is currently being harvested via kinetic energy harvesting system 112, energy harvesting control system 104 may determine that a total of 21W is currently being harvested from person 110.

In some embodiments, determining whether the energy harvested is sufficient to power one or more electronic user devices (block 704) includes determining whether the total amount of energy currently being harvested is greater than or equal to the power required to operate the one or more electronic user devices. For example, if computer 210 requires 10W of power to operate and laptop computer 214 requires 5W of power to operate and both are enabled, energy harvesting control system 104 may determine that a total of 15W is required to operate the devices. In such an embodiment, energy harvesting control system 104 may determine that the 20W that is currently being harvested from person 110 is sufficient to power the devices (e.g., a surplus of 5W exists). If, however, energy harvesting control system 104 determines that a total of 10W is currently being harvested from person 110, energy harvesting control system 104 may determine that the 10W that is currently being harvested from person 110 is not sufficient to power the devices (e.g., an additional 5W is needed).

If it is determined that the energy harvested is sufficient to power one or more electronic user devices, method 700 may proceed to powering the one or more electronic user devices using the harvested energy (block 706). For example, energy harvesting control system 104 may provide 15W of the harvested power to computer 210 and laptop computer 214, and provide for storing the 5W surplus in energy storage device(s) 120 for use at a later time.

If it is determined that the energy harvested is not sufficient to power one or more electronic user devices, method 700 may proceed to powering the one or more electronic user devices using an alternative power source (block 708). For example, energy harvesting control system 104 may use 15W from energy source(s) 122 to power the devices. In some embodiments, alternative power sources can be used in conjunction with the harvested energy. For example, where 5W is being harvested, and 2W can be sourced from energy storage device(s) 120, energy harvesting control system 104 may power the devices using 8W from energy source(s) 122, the 5W that is currently being harvested, and the 2W sourced from energy storage device(s) 120.

It will be appreciated that methods 400, 500, 550 and 700 are exemplary embodiments of methods that may be employed in accordance with techniques described herein. The methods 400, 500, 550 and 700 may be may be modified to facilitate variations of its implementations and uses. The order of the methods 400, 500, 550 and 700 and the operations provided therein may be changed, and various elements may be added, reordered, combined, omitted, modified, etc. The methods 400, 500, 550 and 700 may be implemented in software, hardware, or a combination thereof. Some or all of methods 400, 500, 550 and 700 may be may be implemented by one or more of the modules/applications described herein and/or may be executed on one or more devices. For example, energy harvest control module 1010 may be employed on a single computer/server or multiple computers/servers.

Figure 8:
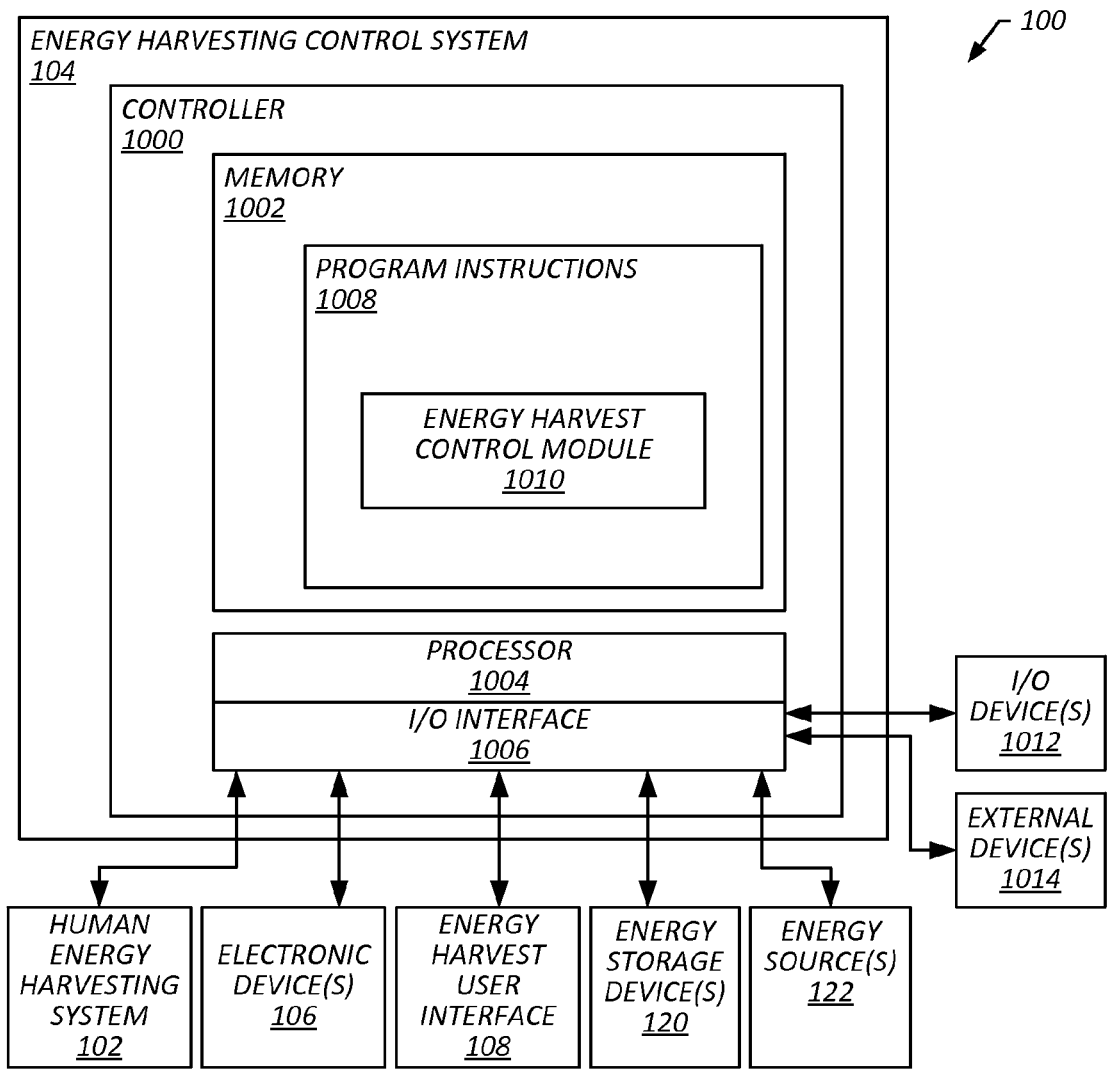
FIG. 8 is a block diagram that illustrates components of an energy harvesting control system in accordance with one more embodiments of the present invention.

FIG. 8 is a block diagram that illustrates system 100 and components of an energy harvesting control system 104 in accordance with one more embodiments of the present invention. In some embodiments, energy harvesting control system 104 includes a controller 1000 for controlling the operational aspects of energy harvesting control system 104. In some embodiments, controller 1000 includes a memory 1002, a processor 1004 and an input/output (I/O) interface 1006. Memory 1002 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. Memory 1002 may include a non-transitory computer readable storage medium having program instructions 1008 stored thereon that are executable by a computer processor (e.g., processor 1004) to cause/perform the functional operations (e.g., methods/routines/processes) described herein (e.g., with regard to human energy harvesting system 102, energy harvesting control system 104, and/or electronic user device (s) 106). Program instructions 1008 may include program instructions modules that are executable by processor 1004 to provide some or all of the functionality described herein with regard to energy harvesting control system 104. Program instructions 1008 may include an energy harvest control module 1010 for performing some or all of the operational aspects of methods 400, 500, 550 and 700.

Processor 1004 may be any suitable processor(s) capable of executing/performing program instructions. Processor 1004 may include a central processing unit (CPU) that carries out program instructions (e.g., program instructions of module 1010) to perform arithmetical, logical, and input/output operations of energy harvesting control system 104, including those described herein. I/O interface 1006 may provide an interface for communication with human energy harvesting system 104, electronic devices 106, energy harvesting user interface 108, energy storage device(s) 120, energy source(s) 122, other I/O device(s) 1012 and/or other external device(s) 1014. I/O devices 1012 may include, for example, a keyboard, a graphical user interface, a microphone, a speaker, and/or the like. External devices 1014 may include, for example, computer devices, network servers, client/user devices, external databases (e.g., an external wellness database), and/or the like. The various devices may be connected to I/O interface 1006 via a wired or wireless connection (e.g., via a wired/wireless electronic communications network).

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification.

As used throughout this application, the word "may" is used in a permissive sense (i.e., meaning having the potential to), rather than the mandatory sense (i.e., meaning must). The words "include", "including", and "includes" mean including, but not limited to. As used throughout this application, the singular forms "a", "an" and "the" include plural referents unless the content clearly indicates otherwise. Thus, for example, reference to "an element" may include a combination of two or more elements. Unless specifically stated otherwise, as apparent from the discussion, it is appreciated that throughout this specification discussions utilizing terms such as "processing", "computing", "calculating", "determining" or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical electronic or magnetic quantities within memories, registers, or other information storage devices, transmission devices, or display devices of the special purpose computer or similar special purpose electronic processing/computing device.

What is claimed is:

1. A workplace energy harvesting system for harvesting energy from an employee, the system comprising:
   one or more electronic user devices;
   a human energy harvesting system comprising:
      a kinetic energy harvesting system comprising one or more kinetic energy harvesting devices configured to harvest kinetic energy generated by physical activity of the employee; and
      a neural energy harvesting system comprising one or more neural energy harvesting devices configured to harvest neural energy generated by neural activity of the employee; and
   an energy harvesting control system configured to:
      determine an amount of energy harvested, the energy harvested comprising a sum total of an amount of the kinetic energy harvested via the kinetic energy harvesting system and an amount of the neural energy harvested via the neural energy harvesting system; and
      selectively enable/disable at least one of the one or more electronic user devices based at least in part on the amount of energy harvested.

2. The system of claim 1, wherein the kinetic energy system comprises a plurality of exercise devices disposed on a floor of the employee's office such that the employee can engage a different exercise device when located at different positions in the office.

3. The system of claim 2, wherein each of the plurality of exercise devices comprise a walking platform such that the employee can engage a different walking platform when located at different positions in the office.

4. The system of claim 2, wherein each of the plurality of exercise devices is associated with a different set of one or more electronic user devices, and wherein operation of a set of electronic user devices is based at least in part on an amount of energy harvested as a result use of the associated exercise device.

5. The system of claim 4, wherein the energy harvesting control system is configured to enable a set of electronic devices associated with an exercise device when an amount of energy generated as a result of use of the exercise device satisfies an energy threshold value, and disable the set of electronic devices associated with the exercise device when the amount of energy generated as a result of use of the exercise device does not satisfy the energy threshold value.

6. The system of claim 1, wherein selectively enabling/disabling one or more electronic user devices based at least in part on the amount of energy harvested comprises:
   determining whether the amount of energy harvested satisfies an energy threshold amount; and
   enabling at least one of the one or more electronic user devices in response to determining that the amount of energy harvested satisfies the energy threshold, and disabling at least one of the one or more electronic user devices in response to determining that the amount of energy harvested does not satisfy the energy threshold amount.

7. The system of claim 6, wherein the energy threshold amount is configured to be modified by the employee.

8. The system of claim 1, wherein the one or more electronic user devices comprise a first set of one or more electronic user devices associated with a first energy threshold amount and a second set of one or more electronic user devices associated with a second energy threshold amount, and wherein selectively enabling/disabling one or more electronic user devices based at least in part on the amount of energy harvested comprises:
   determining whether the amount of energy harvested satisfies the first energy threshold amount, and
   enabling the first set of one or more electronic user devices in response to determining that the amount of energy harvested satisfies the first energy threshold amount, and disabling the first set of one or more electronic user devices in response to determining that the amount of energy harvested does not satisfy the first energy threshold amount; and
   determine whether the amount of energy harvested satisfies the second energy threshold amount, and
   enabling the second set of one or more electronic user devices in response to determining that the amount of energy harvested satisfies the second energy threshold amount, and disabling the second set of one or more electronic user devices in response to determining that the amount of energy harvested does not satisfy the second energy threshold amount.

9. The system of claim 1, wherein the kinetic energy system comprises a piezoelectric transducer configured to harvest power generated by a hip-flexor of the employee.

10. The system of claim 1, wherein the kinetic energy system comprises a fitness/exercise device.

11. The system of claim 1, wherein the neural energy system comprises a neural headset comprising one or more neural energy transducers configured to be disposed about a head of the employee.

12. The system of claim 1, further comprising an energy storage device, wherein the energy harvesting control system is configured to provide for storing at least a portion of the energy harvested in the energy storage device when the energy harvested is not required to power an electronic user device, and to at least partially power an electronic user device using energy stored by the energy storage device.

13. The system of claim 1, further comprising a connection to an electrical power grid, wherein the energy harvesting control system is configured to at least partially power an electronic user device using energy provided via the electrical power grid.

14. The system of claim 1, further comprising an energy storage device and an alternative energy source, wherein the energy harvesting control system is configured to at least partially power an electronic user device simultaneously using at least two of the following: energy stored by the energy storage device, energy currently being provided by the human energy harvest system, and energy provided by the alternative power source.

15. The system of claim 1, further comprising an energy harvest user interface configured to display metrics for energy harvested and status information for the one or more electronic user devices, and a coaching avatar.

16. A system for harvesting human energy from an employee, the system comprising:
  a human energy harvesting system comprising one or more kinetic energy harvesting devices configured to harvest kinetic energy generated by physical activity of the employee, the one or more kinetic energy devices comprising a plurality of walking platforms disposed on a floor of the employee's office such that the employee can engage a different walking platform when located at different positions in the office, a walking platform configured to harvest kinetic energy generated by the employee when walking on the walking platform;
  an energy harvesting control system configured to:
    determine an amount of energy harvested via human energy harvesting system, the amount of energy harvested comprising an amount of energy harvested via the plurality of walking platforms; and
    selectively enable/disable one or more electronic user devices based at least in part on the amount of energy harvested.

17. The system of claim 16, wherein the human energy harvesting system comprises one or more neural energy harvesting devices configured to harvest neural energy generated by neural activity of the employee.

18. The system of claim 16, wherein selectively enabling/disabling one or more electronic user devices based at least in part on the amount of energy harvested comprises:
  determining whether the amount of energy harvested satisfies an energy threshold amount; and
  enabling at least one of the one or more electronic user devices in response to determining that the amount of energy harvested satisfies the energy threshold amount, and disabling at least one of the one or more electronic user devices in response to determining that the amount of energy harvested does not satisfy the energy threshold amount.

19. The system of claim 16, wherein the energy harvesting control system is configured to:
  determine whether an amount of energy generated by use of a walking platform satisfies a walking platform energy threshold amount; and
  enable at least one of one or more electronic user devices associated with the walking platform in response to determining that the amount of energy generated by use of the walking platform satisfies the walking platform energy threshold amount, and disable at least one of one or more electronic user devices associated with the walking platform in response to determining that the amount of energy generated by use of the walking platform does not satisfy the walking platform energy threshold amount.

20. A computer-implemented method for harvesting human energy from an employee, the method comprising:
  determine an amount of energy harvested, the amount of energy harvested comprising:
    an amount of kinetic energy harvested by a kinetic energy system comprising one or more kinetic energy harvesting devices configured to harvest kinetic energy generated by physical activity of an employee; and
    an amount of neural energy harvested by a neural energy system comprising one or more neural energy harvesting devices configured to harvest neural energy generated by neural activity of the employee; and
  selectively enabling/disabling one or more electronic user devices based at least in part on the amount of energy harvested.

21. The method of claim 20, wherein the kinetic energy system comprises a plurality of exercise devices disposed on a floor the employee's office such that the employee can engage a different exercise device when located at different positions in the office.

22. The method of claim 20, wherein selectively enable/disable one or more electronic user devices based at least in part on the amount of energy harvested comprises:
  determining whether the amount of energy harvested satisfies an energy threshold amount; and
  enabling at least one of the one or more electronic user devices in response to determining that the amount of energy harvested satisfies the energy threshold amount.

23. The method of claim 22, wherein selectively enable/disable one or more electronic user devices based at least in part on the amount of energy harvested comprises:
  determining whether the amount of energy harvested satisfies an energy threshold amount; and
  disabling at least one of the one or more electronic user devices in response to determining that the amount of energy harvested does not satisfy the energy threshold amount.

* * * * *